United States Patent
Krizman et al.

(10) Patent No.: US 9,766,246 B2
(45) Date of Patent: *Sep. 19, 2017

(54) SRM/MRM ASSAY FOR SUBTYPING LUNG HISTOLOGY

(71) Applicant: Expression Pathology, Inc., Rockville, MD (US)

(72) Inventors: David B. Krizman, Gaithersburg, MD (US); Wei-Li Liao, Herndon, VA (US); Sheeno Thyparambil, Frederick, MD (US); Todd Hembrough, Gaithersburg, MD (US)

(73) Assignee: Expression Pathology, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/216,789

(22) Filed: Jul. 22, 2016

(65) Prior Publication Data
US 2016/0320398 A1 Nov. 3, 2016

Related U.S. Application Data

(63) Continuation of application No. 14/935,586, filed on Nov. 9, 2015, which is a continuation of application No. 14/543,610, filed on Nov. 17, 2014, now Pat. No. 9,261,506, which is a continuation of application No. PCT/US2013/041424, filed on May 16, 2013.

(60) Provisional application No. 61/647,602, filed on May 16, 2012.

(51) Int. Cl.
*G01N 33/53* (2006.01)
*G01N 33/574* (2006.01)
*G01N 33/68* (2006.01)

(52) U.S. Cl.
CPC . *G01N 33/57492* (2013.01); *G01N 33/57423* (2013.01); *G01N 33/57484* (2013.01); *G01N 33/6848* (2013.01); *G01N 2033/57453* (2013.01); *G01N 2333/47* (2013.01); *G01N 2333/4704* (2013.01); *G01N 2333/4742* (2013.01); *G01N 2333/70596* (2013.01); *G01N 2333/96472* (2013.01); *G01N 2458/15* (2013.01); *G01N 2560/00* (2013.01)

(58) Field of Classification Search
None
See application file for complete search history.

(56) References Cited

U.S. PATENT DOCUMENTS

| | | | |
|---|---|---|---|
| 7,473,532 B2 | 1/2009 | Darfler et al. | |
| 7,501,286 B2 | 3/2009 | Gygi et al. | |
| 7,632,686 B2 | 12/2009 | Anderson | |
| 8,030,083 B2 | 10/2011 | Oda | |
| 8,586,006 B2 | 11/2013 | Hood et al. | |
| 9,091,651 B2 * | 7/2015 | Kearney | G01N 33/6848 |
| 9,261,506 B2 | 2/2016 | Krizman et al. | |
| 2010/0028876 A1 | 2/2010 | Gordon et al. | |
| 2012/0225954 A1 | 9/2012 | Moran et al. | |

FOREIGN PATENT DOCUMENTS

| | | |
|---|---|---|
| CA | 2751835 A1 | 3/2012 |
| WO | 2010030598 A2 | 3/2010 |
| WO | 2011127219 A1 | 10/2011 |
| WO | 2011149943 A1 | 12/2011 |
| WO | WO2012102963 * | 8/2012 |

OTHER PUBLICATIONS

Extended European Search Report in Application No. 13790060.1, mailing date Jan. 14, 2016, 11 pages.

(Continued)

*Primary Examiner* — Jacob Cheu
(74) *Attorney, Agent, or Firm* — Edell, Shapiro & Finnan, LLC.

(57) ABSTRACT

The current disclosure provides for specific peptides, and derived ionization characteristics of the peptides, from the KRT5, KRT7, NapsinA, TTF1, TP63, and/or MUC1 proteins that are particularly advantageous for quantifying the KRT5, KRT7, NapsinA, TTF1, TP63, and/or MUC1 proteins directly in biological samples that have been fixed in formalin by the method of Selected Reaction Monitoring (SRM) mass spectrometry, or what can also be termed as Multiple Reaction Monitoring (MRM) mass spectrometry. Such biological samples are chemically preserved and fixed wherein said biological sample is selected from tissues and cells treated with formaldehyde containing agents/fixatives including formalin-fixed tissue/cells, formalin-fixed/paraffin embedded (FFPE) tissue/cells, FFPE tissue blocks and cells from those blocks, and tissue culture cells that have been formalin fixed and or paraffin embedded. A protein sample is prepared from said biological sample using the Liquid Tissue™ reagents and protocol and the KRT5, KRT7, NapsinA, TTF1, TP63, and/or MUC1 proteins are quantitated in the Liquid Tissue™ sample by the method of SRM/MRM mass spectrometry by quantitating in the protein sample at least one or more of the peptides described. These peptides can be quantitated if they reside in a modified or an unmodified form. An example of a modified form of a KRT5, KRT7, NapsinA, TTF1, TP63, and MUC1 fragment peptide is phosphorylation of a tyrosine, threonine, serine, and/or other amino acid residues within the peptide sequence.

12 Claims, 2 Drawing Sheets

(56) References Cited

OTHER PUBLICATIONS

Geng, M., et al.: "Proteomics of glycoproteins based on affinity selection of glycopeptides from tryptic digests," Journal of Chromatography B, 752:293-306 (2001).

Herbst, R., et al.: "Non-Small Cell Lung Cancer and Antiangiogenic Therapy: What Can Be Expected of Bevacizumab?" The Oncologist, 2004, vol. 9, pp. 19-26.

Hembrough, T., et al.: "Application of Selected Reaction Monitoring for Multiplex Quantification of Clinically Validated Biomarkers in Formalin-Fixed, Paraffin-Embedded Tumor Tissue", The Journal of Molecular Diagnostics (American Society for Investigative Pathology, vol. 15, No. 4, Jul. 4, 2013, pp. 454-465.

International Search Report and Written Opinion in International Application No. PCT/US2013/041424, mailing date Oct. 24, 2013, 10 pages.

\* cited by examiner

FIGURE 2.

| Cancer Type | KR7 | NapsinA | TTF1 | MUC1 | KR5 | TP63 |
|---|---|---|---|---|---|---|
| Adenocarcinoma | ← | ← | ← | ← | → | → |
| Squamous Cell Carcinoma | → | → | → | → | ← | ← |

SEQUENCE LISTING

<160> NUMBER OF SEQ ID NOS: 17

<210> SEQ ID NO 1
<211> LENGTH: 9
<212> TYPE: PRT
<213> ORGANISM: Homo sapiens

<400> SEQUENCE: 1

Ala Gln Tyr Glu Glu Ile Ala Asn Arg
1               5

<210> SEQ ID NO 2
<211> LENGTH: 11
<212> TYPE: PRT
<213> ORGANISM: Homo sapiens

<400> SEQUENCE: 2

Ile Ser Ile Ser Thr Ser Gly Gly Ser Phe Arg
1               5                   10

<210> SEQ ID NO 3
<211> LENGTH: 13
<212> TYPE: PRT
<213> ORGANISM: Homo sapiens

<400> SEQUENCE: 3

Leu Pro Asp Ile Phe Glu Ala Gln Ile Ala Gly Leu Arg
1               5                   10

<210> SEQ ID NO 4
<211> LENGTH: 12
<212> TYPE: PRT
<213> ORGANISM: Homo sapiens

<400> SEQUENCE: 4

Ser Leu Asp Leu Asp Gly Ile Ile Ala Glu Val Lys
1               5                   10

<210> SEQ ID NO 5
<211> LENGTH: 9
<212> TYPE: PRT
<213> ORGANISM: Homo sapiens

<400> SEQUENCE: 5

Phe Ala Ile Gln Tyr Gly Thr Gly Arg
1               5

<210> SEQ ID NO 6
<211> LENGTH: 11
<212> TYPE: PRT
<213> ORGANISM: Homo sapiens

<400> SEQUENCE: 6

Gln Gly Gly Phe Leu Gly Leu Ser Asn Ile Lys
1               5                   10

<210> SEQ ID NO 7
<211> LENGTH: 9
<212> TYPE: PRT
<213> ORGANISM: Homo sapiens

<400> SEQUENCE: 7

Ser Ser Val Pro Ser Ser Thr Glu Lys
1               5

<210> SEQ ID NO 8
<211> LENGTH: 6
<212> TYPE: PRT
<213> ORGANISM: Homo sapiens

<400> SEQUENCE: 8

Phe Pro Ala Ile Ser Arg
1               5

<210> SEQ ID NO 9
<211> LENGTH: 8
<212> TYPE: PRT
<213> ORGANISM: Homo sapiens

<400> SEQUENCE: 9

Val Ala Val Pro Val Leu Val Lys
1               5

<210> SEQ ID NO 10
<211> LENGTH: 6
<212> TYPE: PRT
<213> ORGANISM: Homo sapiens

<400> SEQUENCE: 10

Ile Pro Glu Gln Phe Arg
1               5

<210> SEQ ID NO 11
<211> LENGTH: 16
<212> TYPE: PRT
<213> ORGANISM: Homo sapiens

<400> SEQUENCE: 11

Thr Pro Ser Ser Ala Ser Thr Val Ser Val Gly Ser Ser Glu Thr Arg
1               5                   10                  15

<210> SEQ ID NO 12
<211> LENGTH: 590
<212> TYPE: PRT
<213> ORGANISM: Homo sapiens

<400> SEQUENCE: 12

Met Ser Arg Gln Ser Ser Val Ser Phe Arg Ser Gly Gly Ser Arg Ser
1               5                   10                  15

Phe Ser Thr Ala Ser Ala Ile Thr Pro Ser Val Ser Arg Thr Ser Phe
                20                  25                  30

Thr Ser Val Ser Arg Ser Gly Gly Gly Gly Gly Gly Phe Gly Arg
            35                  40                  45

Val Ser Leu Ala Gly Ala Cys Gly Val Gly Gly Tyr Gly Ser Arg Ser
        50                  55                  60

Leu Tyr Asn Leu Gly Gly Ser Lys Arg Ile Ser Ile Ser Thr Ser Gly
65                  70                  75                  80

Gly Ser Phe Arg Asn Arg Phe Gly Ala Gly Ala Gly Gly Gly Tyr Gly
                85                  90                  95

Phe Gly Gly Gly Ala Gly Ser Gly Phe Gly Phe Gly Gly Gly Ala Gly
                100                 105                 110

Gly Gly Phe Gly Leu Gly Gly Gly Ala Gly Phe Gly Gly Gly Phe Gly
            115                 120                 125

Gly Pro Gly Phe Pro Val Cys Pro Pro Gly Gly Ile Gln Glu Val Thr
        130                 135                 140

```
Val Asn Gln Ser Leu Leu Thr Pro Leu Asn Leu Gln Ile Asp Pro Ser
145                 150                 155                 160

Ile Gln Arg Val Arg Thr Glu Arg Glu Gln Ile Lys Thr Leu Asn
            165                 170                 175

Asn Lys Phe Ala Ser Phe Ile Asp Lys Val Arg Phe Leu Glu Gln Gln
                180                 185                 190

Asn Lys Val Leu Asp Thr Lys Trp Thr Leu Leu Gln Glu Gln Gly Thr
            195                 200                 205

Lys Thr Val Arg Gln Asn Leu Glu Pro Leu Phe Glu Gln Tyr Ile Asn
    210                 215                 220

Asn Leu Arg Arg Gln Leu Asp Ser Ile Val Gly Glu Arg Gly Arg Leu
225                 230                 235                 240

Asp Ser Glu Leu Arg Asn Met Gln Asp Leu Val Glu Asp Phe Lys Asn
                245                 250                 255

Lys Tyr Glu Asp Glu Ile Asn Lys Arg Thr Thr Ala Glu Asn Glu Phe
                260                 265                 270

Val Met Leu Lys Lys Asp Val Asp Ala Ala Tyr Met Asn Lys Val Glu
            275                 280                 285

Leu Glu Ala Lys Val Asp Ala Leu Met Asp Glu Ile Asn Phe Met Lys
    290                 295                 300

Met Phe Phe Asp Ala Glu Leu Ser Gln Met Gln Thr His Val Ser Asp
305                 310                 315                 320

Thr Ser Val Val Leu Ser Met Asp Asn Asn Arg Asn Leu Asp Leu Asp
                325                 330                 335

Ser Ile Ile Ala Glu Val Lys Ala Gln Tyr Glu Glu Ile Ala Asn Arg
                340                 345                 350

Ser Arg Thr Glu Ala Glu Ser Trp Tyr Gln Thr Lys Tyr Glu Glu Leu
            355                 360                 365

Gln Gln Thr Ala Gly Arg His Gly Asp Asp Leu Arg Asn Thr Lys His
    370                 375                 380

Glu Ile Ser Glu Met Asn Arg Met Ile Gln Arg Leu Arg Ala Glu Ile
385                 390                 395                 400

Asp Asn Val Lys Lys Gln Cys Ala Asn Leu Gln Asn Ala Ile Ala Asp
                405                 410                 415

Ala Glu Gln Arg Gly Glu Leu Ala Leu Lys Asp Ala Arg Asn Lys Leu
            420                 425                 430

Ala Glu Leu Glu Glu Ala Leu Gln Lys Ala Lys Gln Asp Met Ala Arg
    435                 440                 445

Leu Leu Arg Glu Tyr Gln Glu Leu Met Asn Thr Lys Leu Ala Leu Asp
    450                 455                 460

Val Glu Ile Ala Thr Tyr Arg Lys Leu Leu Glu Gly Glu Glu Cys Arg
465                 470                 475                 480

Leu Ser Gly Glu Gly Val Gly Pro Val Asn Ile Ser Val Val Thr Ser
            485                 490                 495

Ser Val Ser Ser Gly Tyr Gly Ser Gly Ser Gly Tyr Gly Gly Gly Leu
            500                 505                 510

Gly Gly Gly Leu Gly Gly Gly Leu Gly Gly Gly Leu Ala Gly Gly Ser
            515                 520                 525

Ser Gly Ser Tyr Tyr Ser Ser Ser Ser Gly Gly Val Gly Leu Gly Gly
            530                 535                 540

Gly Leu Ser Val Gly Gly Ser Gly Phe Ser Ala Ser Ser Gly Arg Gly
545                 550                 555                 560

Leu Gly Val Gly Phe Gly Ser Gly Gly Gly Ser Ser Ser Ser Val Lys
```

```
                         565                 570                 575
Phe Val Ser Thr Thr Ser Ser Ser Arg Lys Ser Phe Lys Ser
                580                 585                 590

<210> SEQ ID NO 13
<211> LENGTH: 469
<212> TYPE: PRT
<213> ORGANISM: Homo sapiens

<400> SEQUENCE: 13

Met Ser Ile His Phe Ser Ser Pro Val Phe Thr Ser Arg Ser Ala Ala
1               5                   10                  15

Phe Ser Gly Arg Gly Ala Gln Val Arg Leu Ser Ser Ala Arg Pro Gly
            20                  25                  30

Gly Leu Gly Ser Ser Ser Leu Tyr Gly Leu Gly Ala Ser Arg Pro Arg
        35                  40                  45

Val Ala Val Arg Ser Ala Tyr Gly Gly Pro Val Gly Ala Gly Ile Arg
    50                  55                  60

Glu Val Thr Ile Asn Gln Ser Leu Leu Ala Pro Leu Arg Leu Asp Ala
65                  70                  75                  80

Asp Pro Ser Leu Gln Arg Val Arg Gln Glu Ser Glu Gln Ile Lys
                85                  90                  95

Thr Leu Asn Asn Lys Phe Ala Ser Phe Ile Asp Lys Val Arg Phe Leu
            100                 105                 110

Glu Gln Gln Asn Lys Leu Leu Glu Thr Lys Trp Thr Leu Leu Gln Glu
        115                 120                 125

Gln Lys Ser Ala Lys Ser Ser Arg Leu Pro Asp Ile Phe Glu Ala Gln
    130                 135                 140

Ile Ala Gly Leu Arg Gly Gln Leu Glu Ala Leu Gln Val Asp Gly Gly
145                 150                 155                 160

Arg Leu Glu Ala Glu Leu Arg Ser Met Gln Asp Val Val Glu Asp Phe
                165                 170                 175

Lys Asn Lys Tyr Glu Asp Glu Ile Asn His Arg Thr Ala Ala Glu Asn
            180                 185                 190

Glu Phe Val Val Leu Lys Lys Asp Val Asp Ala Ala Tyr Met Ser Lys
        195                 200                 205

Val Glu Leu Glu Ala Lys Val Asp Ala Leu Asn Asp Glu Ile Asn Phe
    210                 215                 220

Leu Arg Thr Leu Asn Glu Thr Glu Leu Thr Glu Leu Gln Ser Gln Ile
225                 230                 235                 240

Ser Asp Thr Ser Val Val Leu Ser Met Asp Asn Ser Arg Ser Leu Asp
                245                 250                 255

Leu Asp Gly Ile Ile Ala Glu Val Lys Ala Gln Tyr Glu Glu Met Ala
            260                 265                 270

Lys Cys Ser Arg Ala Glu Ala Glu Ala Trp Tyr Gln Thr Lys Phe Glu
        275                 280                 285

Thr Leu Gln Ala Gln Ala Gly Lys His Gly Asp Asp Leu Arg Asn Thr
    290                 295                 300

Arg Asn Glu Ile Ser Glu Met Asn Arg Ala Ile Gln Arg Leu Gln Ala
305                 310                 315                 320

Glu Ile Asp Asn Ile Lys Asn Gln Arg Ala Lys Leu Glu Ala Ala Ile
                325                 330                 335

Ala Glu Ala Glu Glu Arg Gly Glu Leu Ala Leu Lys Asp Ala Arg Ala
            340                 345                 350
```

-continued

```
Lys Gln Glu Glu Leu Glu Ala Leu Gln Arg Gly Lys Gln Asp Met
            355                 360                 365
Ala Arg Gln Leu Arg Glu Tyr Gln Glu Leu Met Ser Val Lys Leu Ala
370                 375                 380
Leu Asp Ile Glu Ile Ala Thr Tyr Arg Lys Leu Leu Glu Gly Glu Glu
385                 390                 395                 400
Ser Arg Leu Ala Gly Asp Gly Val Gly Ala Val Asn Ile Ser Val Met
                405                 410                 415
Asn Ser Thr Gly Gly Ser Ser Ser Gly Gly Ile Gly Leu Thr Leu
            420                 425                 430
Gly Gly Thr Met Gly Ser Asn Ala Leu Ser Phe Ser Ser Ser Ala Gly
            435                 440                 445
Pro Gly Leu Leu Lys Ala Tyr Ser Ile Arg Thr Ala Ser Ala Ser Arg
            450                 455                 460
Arg Ser Ala Arg Asp
465

<210> SEQ ID NO 14
<211> LENGTH: 420
<212> TYPE: PRT
<213> ORGANISM: Homo sapiens

<400> SEQUENCE: 14

Met Ser Pro Pro Leu Leu Gln Pro Leu Leu Leu Leu Leu Pro Leu
1               5                   10                  15
Leu Asn Val Glu Pro Ser Gly Ala Thr Leu Ile Arg Ile Pro Leu His
                20                  25                  30
Arg Val Gln Pro Gly Arg Arg Ile Leu Asn Leu Leu Arg Gly Trp Arg
            35                  40                  45
Glu Pro Ala Glu Leu Pro Lys Leu Gly Ala Pro Ser Pro Gly Asp Lys
        50                  55                  60
Pro Ile Phe Val Pro Leu Ser Asn Tyr Arg Asp Val Gln Tyr Phe Gly
65                  70                  75                  80
Glu Ile Gly Leu Gly Thr Pro Pro Gln Asn Phe Thr Val Ala Phe Asp
                85                  90                  95
Thr Gly Ser Ser Asn Leu Trp Val Pro Ser Arg Arg Cys His Phe Phe
            100                 105                 110
Ser Val Pro Cys Trp Leu His His Arg Phe Asp Pro Lys Ala Ser Ser
        115                 120                 125
Ser Phe Gln Ala Asn Gly Thr Lys Phe Ala Ile Gln Tyr Gly Thr Gly
    130                 135                 140
Arg Val Asp Gly Ile Leu Ser Glu Asp Lys Leu Thr Ile Gly Gly Ile
145                 150                 155                 160
Lys Gly Ala Ser Val Ile Phe Gly Glu Ala Leu Trp Glu Pro Ser Leu
                165                 170                 175
Val Phe Ala Phe Ala His Phe Asp Gly Ile Leu Gly Leu Gly Phe Pro
            180                 185                 190
Ile Leu Ser Val Glu Gly Val Arg Pro Pro Met Asp Val Leu Val Glu
        195                 200                 205
Gln Gly Leu Leu Asp Lys Pro Val Phe Ser Phe Tyr Leu Asn Arg Asp
    210                 215                 220
Pro Glu Glu Pro Asp Gly Gly Glu Leu Val Leu Gly Gly Ser Asp Pro
225                 230                 235                 240
Ala His Tyr Ile Pro Pro Leu Thr Phe Val Pro Val Thr Val Pro Ala
                245                 250                 255
```

-continued

```
Tyr Trp Gln Ile His Met Glu Arg Val Lys Val Gly Pro Gly Leu Thr
            260                 265                 270

Leu Cys Ala Lys Gly Cys Ala Ala Ile Leu Asp Thr Gly Thr Ser Leu
        275                 280                 285

Ile Thr Gly Pro Thr Glu Glu Ile Arg Ala Leu His Ala Ala Ile Gly
290                 295                 300

Gly Ile Pro Leu Leu Ala Gly Glu Tyr Ile Ile Leu Cys Ser Glu Ile
305                 310                 315                 320

Pro Lys Leu Pro Ala Val Ser Phe Leu Leu Gly Gly Val Trp Phe Asn
                325                 330                 335

Leu Thr Ala His Asp Tyr Val Ile Gln Thr Thr Arg Asn Gly Val Arg
            340                 345                 350

Leu Cys Leu Ser Gly Phe Gln Ala Leu Asp Val Pro Pro Pro Ala Gly
        355                 360                 365

Pro Phe Trp Ile Leu Gly Asp Val Phe Leu Gly Thr Tyr Val Ala Val
370                 375                 380

Phe Asp Arg Gly Asp Met Lys Ser Ser Ala Arg Val Gly Leu Ala Arg
385                 390                 395                 400

Ala Arg Thr Arg Gly Ala Asp Leu Gly Trp Gly Glu Thr Ala Gln Ala
                405                 410                 415

Gln Phe Pro Gly
            420

<210> SEQ ID NO 15
<211> LENGTH: 1254
<212> TYPE: PRT
<213> ORGANISM: Homo sapiens

<400> SEQUENCE: 15

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
```

```
                195                 200                 205
Gly Ser Thr Ala Pro Pro Ala His Gly Val Thr Ser Ala Pro Asp Thr
210                 215                 220
Arg Pro Ala Pro Gly Ser Thr Ala Pro Pro Ala His Gly Val Thr Ser
225                 230                 235                 240
Ala Pro Asp Thr Arg Pro Ala Pro Gly Ser Thr Ala Pro Pro Ala His
                245                 250                 255
Gly Val Thr Ser Ala Pro Asp Thr Arg Pro Ala Pro Gly Ser Thr Ala
                260                 265                 270
Pro Pro Ala His Gly Val Thr Ser Ala Pro Asp Thr Arg Pro Ala Pro
                275                 280                 285
Gly Ser Thr Ala Pro Pro Ala His Gly Val Thr Ser Ala Pro Asp Thr
290                 295                 300
Arg Pro Ala Pro Gly Ser Thr Ala Pro Pro Ala His Gly Val Thr Ser
305                 310                 315                 320
Ala Pro Asp Thr Arg Pro Ala Pro Gly Ser Thr Ala Pro Pro Ala His
                325                 330                 335
Gly Val Thr Ser Ala Pro Asp Thr Arg Pro Ala Pro Gly Ser Thr Ala
                340                 345                 350
Pro Pro Ala His Gly Val Thr Ser Ala Pro Asp Thr Arg Pro Ala Pro
                355                 360                 365
Gly Ser Thr Ala Pro Pro Ala His Gly Val Thr Ser Ala Pro Asp Thr
370                 375                 380
Arg Pro Ala Pro Gly Ser Thr Ala Pro Pro Ala His Gly Val Thr Ser
385                 390                 395                 400
Ala Pro Asp Thr Arg Pro Ala Pro Gly Ser Thr Ala Pro Pro Ala His
                405                 410                 415
Gly Val Thr Ser Ala Pro Asp Thr Arg Pro Ala Pro Gly Ser Thr Ala
                420                 425                 430
Pro Pro Ala His Gly Val Thr Ser Ala Pro Asp Thr Arg Pro Ala Pro
                435                 440                 445
Gly Ser Thr Ala Pro Pro Ala His Gly Val Thr Ser Ala Asp Thr Arg
450                 455                 460
Pro Ala Pro Gly Ser Thr Ala Pro Pro Ala His Gly Val Thr Ser Ala
465                 470                 475                 480
Pro Asp Thr Arg Pro Ala Pro Gly Ser Thr Ala Pro Pro Ala His Gly
                485                 490                 495
Val Thr Ser Ala Pro Asp Thr Arg Pro Ala Pro Gly Ser Thr Ala Pro
                500                 505                 510
Pro Ala His Gly Val Thr Ser Ala Pro Asp Thr Arg Pro Ala Pro Gly
                515                 520                 525
Ser Thr Ala Pro Pro Ala His Gly Val Thr Ser Ala Pro Asp Thr Arg
                530                 535                 540
Pro Ala Pro Gly Ser Thr Ala Pro Pro Ala His Gly Val Thr Ser Ala
545                 550                 555                 560
Pro Asp Thr Arg Pro Ala Pro Gly Ser Thr Ala Pro Pro Ala His Gly
                565                 570                 575
Val Thr Ser Ala Pro Asp Thr Arg Pro Ala Pro Gly Ser Thr Ala Pro
                580                 585                 590
Pro Ala His Gly Val Thr Ser Ala Pro Asp Thr Arg Pro Ala Pro Gly
                595                 600                 605
Ser Thr Ala Pro Pro Ala His Gly Val Thr Ser Ala Pro Asp Thr Arg
                610                 615                 620
```

```
Pro Ala Pro Gly Ser Thr Ala Pro Ala His Gly Val Thr Ser Ala
625                 630                 635                 640

Pro Asp Thr Arg Pro Ala Pro Gly Ser Thr Ala Pro Ala His Gly
            645                 650                 655

Val Thr Ser Ala Pro Asp Thr Arg Pro Ala Pro Gly Ser Thr Ala Pro
        660                 665                 670

Pro Ala His Gly Val Thr Ser Ala Pro Asp Thr Arg Pro Ala Pro Gly
            675                 680                 685

Ser Thr Ala Pro Pro Ala His Gly Val Thr Ser Ala Pro Asp Thr Arg
        690                 695                 700

Pro Ala Pro Gly Ser Thr Ala Pro Pro Ala His Gly Val Thr Ser Ala
705                 710                 715                 720

Pro Asp Thr Arg Pro Ala Pro Gly Ser Thr Ala Pro Pro Ala His Gly
            725                 730                 735

Val Thr Ser Ala Pro Asp Thr Arg Pro Ala Pro Gly Ser Thr Ala Pro
        740                 745                 750

Pro Ala His Gly Val Thr Ser Ala Pro Asp Thr Arg Pro Ala Pro Gly
            755                 760                 765

Ser Thr Ala Pro Pro Ala His Gly Val Thr Ser Ala Pro Asp Thr Arg
        770                 775                 780

Pro Ala Pro Gly Ser Thr Ala Pro Pro Ala His Gly Val Thr Ser Ala
785                 790                 795                 800

Pro Asp Thr Arg Pro Ala Pro Gly Ser Thr Ala Pro Pro Ala His Gly
            805                 810                 815

Val Thr Ser Ala Pro Asp Thr Arg Pro Ala Pro Gly Ser Thr Ala Pro
        820                 825                 830

Pro Ala His Gly Val Thr Ser Ala Pro Asp Thr Arg Pro Ala Pro Gly
            835                 840                 845

Ser Thr Ala Pro Pro Ala His Gly Val Thr Ser Ala Pro Asp Thr Arg
        850                 855                 860

Pro Ala Pro Gly Ser Thr Ala Pro Pro Ala His Gly Val Thr Ser Ala
865                 870                 875                 880

Pro Asp Thr Arg Pro Ala Pro Gly Ser Thr Ala Pro Pro Ala His Gly
            885                 890                 895

Val Thr Ser Ala Pro Asp Thr Arg Pro Ala Pro Gly Ser Thr Ala Pro
        900                 905                 910

Pro Ala His Gly Val Thr Ser Ala Pro Asp Thr Arg Pro Ala Pro Gly
            915                 920                 925

Ser Thr Ala Pro Pro Ala His Gly Val Thr Ser Ala Pro Asp Asn Arg
        930                 935                 940

Pro Ala Leu Gly Ser Thr Ala Pro Pro Val His Asn Val Thr Ser Ala
945                 950                 955                 960

Ser Gly Ser Ala Ser Gly Ser Ala Ser Thr Leu Val His Asn Gly Thr
            965                 970                 975

Ser Ala Arg Ala Thr Thr Thr Pro Ala Ser Lys Ser Thr Pro Phe Ser
        980                 985                 990

Ile Pro Ser His His Ser Asp Thr Pro Thr Thr Leu Ala Ser His Ser
            995                 1000                1005

Thr Lys Thr Asp Ala Ser Ser Thr His His Ser Ser Val Pro Pro
        1010                1015                1020

Leu Thr Ser Ser Asn His Ser Thr Ser Pro Gln Leu Ser Thr Gly
        1025                1030                1035
```

```
Val Ser Phe Phe Phe Leu Ser Phe His Ile Ser Asn Leu Gln Phe
    1040                1045                1050

Asn Ser Ser Leu Glu Asp Pro Ser Thr Asp Tyr Tyr Gln Glu Leu
    1055                1060                1065

Gln Arg Asp Ile Ser Glu Met Phe Leu Gln Ile Tyr Lys Gln Gly
    1070                1075                1080

Gly Phe Leu Gly Leu Ser Asn Ile Lys Phe Arg Pro Gly Ser Val
    1085                1090                1095

Val Val Gln Leu Thr Leu Ala Phe Arg Glu Gly Thr Ile Asn Val
    1100                1105                1110

His Asp Val Glu Thr Gln Phe Asn Gln Tyr Lys Thr Glu Ala Ala
    1115                1120                1125

Ser Arg Tyr Asn Leu Thr Ile Ser Asp Val Ser Val Ser Asp Val
    1130                1135                1140

Pro Phe Pro Phe Ser Ala Gln Ser Gly Ala Gly Val Pro Gly Trp
    1145                1150                1155

Gly Ile Ala Leu Leu Val Leu Val Cys Val Leu Val Ala Leu Ala
    1160                1165                1170

Ile Val Tyr Leu Ile Ala Leu Ala Val Cys Gln Cys Arg Arg Lys
    1175                1180                1185

Asn Tyr Gly Gln Leu Asp Ile Phe Pro Ala Arg Asp Thr Tyr His
    1190                1195                1200

Pro Met Ser Glu Tyr Pro Thr Tyr His Thr His Gly Arg Tyr Val
    1205                1210                1215

Pro Pro Ser Ser Thr Asp Arg Ser Pro Tyr Glu Lys Val Ser Ala
    1220                1225                1230

Gly Asn Gly Gly Ser Ser Leu Ser Tyr Thr Asn Pro Ala Val Ala
    1235                1240                1245

Ala Thr Ser Ala Asn Leu
    1250

<210> SEQ ID NO 16
<211> LENGTH: 371
<212> TYPE: PRT
<213> ORGANISM: Homo sapiens

<400> SEQUENCE: 16

Met Ser Met Ser Pro Lys His Thr Thr Pro Phe Ser Val Ser Asp Ile
1               5                   10                  15

Leu Ser Pro Leu Glu Glu Ser Tyr Lys Lys Val Gly Met Glu Gly Gly
                20                  25                  30

Gly Leu Gly Ala Pro Leu Ala Ala Tyr Arg Gln Gly Gln Ala Ala Pro
            35                  40                  45

Pro Thr Ala Ala Met Gln Gln His Ala Val Gly His His Gly Ala Val
        50                  55                  60

Thr Ala Ala Tyr His Met Thr Ala Ala Gly Val Pro Gln Leu Ser His
65                  70                  75                  80

Ser Ala Val Gly Gly Tyr Cys Asn Gly Asn Leu Gly Asn Met Ser Glu
                85                  90                  95

Leu Pro Pro Tyr Gln Asp Thr Met Arg Asn Ser Ala Ser Gly Pro Gly
                100                 105                 110

Trp Tyr Gly Ala Asn Pro Asp Pro Arg Phe Pro Ala Ile Ser Arg Phe
            115                 120                 125

Met Gly Pro Ala Ser Gly Met Asn Met Ser Gly Met Gly Gly Leu Gly
        130                 135                 140
```

```
Ser Leu Gly Asp Val Ser Lys Asn Met Ala Pro Leu Pro Ser Ala Pro
145                 150                 155                 160

Arg Arg Lys Arg Val Leu Phe Ser Gln Ala Gln Val Tyr Glu Leu
            165                 170                 175

Glu Arg Arg Phe Lys Gln Gln Lys Tyr Leu Ser Ala Pro Glu Arg Glu
            180                 185                 190

His Leu Ala Ser Met Ile His Leu Thr Pro Thr Gln Val Lys Ile Trp
            195                 200                 205

Phe Gln Asn His Arg Tyr Lys Met Lys Arg Gln Ala Lys Asp Lys Ala
            210                 215                 220

Ala Gln Gln Gln Leu Gln Gln Asp Ser Gly Gly Gly Gly Gly Gly Gly
225                 230                 235                 240

Gly Thr Gly Cys Pro Gln Gln Gln Ala Gln Gln Ser Pro Arg
            245                 250                 255

Arg Val Ala Val Pro Val Leu Val Lys Asp Gly Lys Pro Cys Gln Ala
            260                 265                 270

Gly Ala Pro Ala Pro Gly Ala Ala Ser Leu Gln Gly His Ala Gln Gln
            275                 280                 285

Gln Ala Gln His Gln Ala Gln Ala Ala Gln Ala Ala Ala Ala Ile
            290                 295                 300

Ser Val Gly Ser Gly Gly Ala Gly Leu Gly Ala His Pro Gly His Gln
305                 310                 315                 320

Pro Gly Ser Ala Gly Gln Ser Pro Asp Leu Ala His His Ala Ala Ser
            325                 330                 335

Pro Ala Ala Leu Gln Gly Gln Val Ser Ser Leu Ser His Leu Asn Ser
            340                 345                 350

Ser Gly Ser Asp Tyr Gly Thr Met Ser Cys Ser Thr Leu Leu Tyr Gly
            355                 360                 365

Arg Thr Trp
    370

<210> SEQ ID NO 17
<211> LENGTH: 680
<212> TYPE: PRT
<213> ORGANISM: Homo sapiens

<400> SEQUENCE: 17

Met Asn Phe Glu Thr Ser Arg Cys Ala Thr Leu Gln Tyr Cys Pro Asp
1               5                   10                  15

Pro Tyr Ile Gln Arg Phe Val Glu Thr Pro Ala His Phe Ser Trp Lys
            20                  25                  30

Glu Ser Tyr Tyr Arg Ser Thr Met Ser Gln Ser Thr Gln Thr Asn Glu
            35                  40                  45

Phe Leu Ser Pro Glu Val Phe Gln His Ile Trp Asp Phe Leu Glu Gln
50                  55                  60

Pro Ile Cys Ser Val Gln Pro Ile Asp Leu Asn Phe Val Asp Glu Pro
65                  70                  75                  80

Ser Glu Asp Gly Ala Thr Asn Lys Ile Glu Ile Ser Met Asp Cys Ile
            85                  90                  95

Arg Met Gln Asp Ser Asp Leu Ser Asp Pro Met Trp Pro Gln Tyr Thr
            100                 105                 110

Asn Leu Gly Leu Leu Asn Ser Met Asp Gln Gln Ile Gln Asn Gly Ser
            115                 120                 125

Ser Ser Thr Ser Pro Tyr Asn Thr Asp His Ala Gln Asn Ser Val Thr
```

-continued

```
            130                 135                 140
Ala Pro Ser Pro Tyr Ala Gln Pro Ser Ser Thr Phe Asp Ala Leu Ser
145                 150                 155                 160

Pro Ser Pro Ala Ile Pro Ser Asn Thr Asp Tyr Pro Gly Pro His Ser
                165                 170                 175

Phe Asp Val Ser Phe Gln Gln Ser Ser Thr Ala Lys Ser Ala Thr Trp
            180                 185                 190

Thr Tyr Ser Thr Glu Leu Lys Lys Leu Tyr Cys Gln Ile Ala Lys Thr
        195                 200                 205

Cys Pro Ile Gln Ile Lys Val Met Thr Pro Pro Gln Gly Ala Val
210                 215                 220

Ile Arg Ala Met Pro Val Tyr Lys Lys Ala Glu His Val Thr Glu Val
225                 230                 235                 240

Val Lys Arg Cys Pro Asn His Glu Leu Ser Arg Glu Phe Asn Glu Gly
                245                 250                 255

Gln Ile Ala Pro Pro Ser His Leu Ile Arg Val Glu Gly Asn Ser His
            260                 265                 270

Ala Gln Tyr Val Glu Asp Pro Ile Thr Gly Arg Gln Ser Val Leu Val
        275                 280                 285

Pro Tyr Glu Pro Pro Gln Val Gly Thr Glu Phe Thr Thr Val Leu Tyr
290                 295                 300

Asn Phe Met Cys Asn Ser Ser Cys Val Gly Gly Met Asn Arg Arg Pro
305                 310                 315                 320

Ile Leu Ile Ile Val Thr Leu Glu Thr Arg Asp Gly Gln Val Leu Gly
                325                 330                 335

Arg Arg Cys Phe Glu Ala Arg Ile Cys Ala Cys Pro Gly Arg Asp Arg
            340                 345                 350

Lys Ala Asp Glu Asp Ser Ile Arg Lys Gln Gln Val Ser Asp Ser Thr
        355                 360                 365

Lys Asn Gly Asp Gly Thr Lys Arg Pro Phe Arg Gln Asn Thr His Gly
370                 375                 380

Ile Gln Met Thr Ser Ile Lys Lys Arg Arg Ser Pro Asp Asp Glu Leu
385                 390                 395                 400

Leu Tyr Leu Pro Val Arg Gly Arg Glu Thr Tyr Glu Met Leu Leu Lys
                405                 410                 415

Ile Lys Glu Ser Leu Glu Leu Met Gln Tyr Leu Pro Gln His Thr Ile
            420                 425                 430

Glu Thr Tyr Arg Gln Gln Gln Gln Gln His Gln His Leu Leu Gln
        435                 440                 445

Lys Gln Thr Ser Ile Gln Ser Pro Ser Ser Tyr Gly Asn Ser Ser Pro
450                 455                 460

Pro Leu Asn Lys Met Asn Ser Met Asn Lys Leu Pro Ser Val Ser Gln
465                 470                 475                 480

Leu Ile Asn Pro Gln Gln Arg Asn Ala Leu Thr Pro Thr Thr Ile Pro
                485                 490                 495

Asp Gly Met Gly Ala Asn Ile Pro Met Met Gly Thr His Met Pro Met
            500                 505                 510

Ala Gly Asp Met Asn Gly Leu Ser Pro Thr Gln Ala Leu Pro Pro Pro
        515                 520                 525

Leu Ser Met Pro Ser Thr Ser His Cys Thr Pro Pro Pro Pro Tyr Pro
530                 535                 540

Thr Asp Cys Ser Ile Val Ser Phe Leu Ala Arg Leu Gly Cys Ser Ser
545                 550                 555                 560
```

```
Cys Leu Asp Tyr Phe Thr Thr Gln Gly Leu Thr Thr Ile Tyr Gln Ile
                565                 570                 575

Glu His Tyr Ser Met Asp Asp Leu Ala Ser Leu Lys Ile Pro Glu Gln
            580                 585                 590

Phe Arg His Ala Ile Trp Lys Gly Ile Leu Asp His Arg Gln Leu His
        595                 600                 605

Glu Phe Ser Ser Pro Ser His Leu Leu Arg Thr Pro Ser Ser Ala Ser
        610                 615                 620

Thr Val Ser Val Gly Ser Ser Glu Thr Arg Gly Glu Arg Val Ile Asp
625                 630                 635                 640

Ala Val Arg Phe Thr Leu Arg Gln Thr Ile Ser Phe Pro Pro Arg Asp
                645                 650                 655

Glu Trp Asn Asp Phe Asn Phe Asp Met Asp Ala Arg Arg Asn Lys Gln
            660                 665                 670

Gln Arg Ile Lys Glu Glu Gly Glu
            675                 680
```

SRM/MRM ASSAY FOR SUBTYPING LUNG HISTOLOGY

This application is a continuation of U.S. patent application Ser. No. 14/935,586, filed Nov. 9, 2015, which is a continuation of U.S. patent application Ser. No. 14/543,610, filed Nov. 17, 2014, which is a continuation of International Application No. PCT/US13/41424, filed May 16, 2013, which claims the benefit of U.S. Provisional Application No. 61/647,602, filed May 15, 2012, each of which are entitled "SRM/MRM Assay for the Insulin Receptor Protein," the contents of each of which are hereby incorporated by referenced in their entireties. This application also contains a sequence listing submitted electronically via EFS-web, which serves as both the paper copy and the computer readable form (CRF) and consists of a file entitled "001152_8030_US03_SEQ_LISTING", which was created on Jul. 21, 2016, which is 34,826 bytes in size, and which is also incorporated by reference in its entirety.

INTRODUCTION

Lung cancer is the most prevalent cancer (>200,000 new US cases/year) and has a low five-year survival rate (~15%). Therapy for lung cancer is transitioning from use of a limited selection of therapies consisting of radiation, folate metabolism, platinum-based drugs, and/or taxol-based drugs to more targeted treatments that require histological characterization of the tumor and/or the presence or absence of key biomarker or therapeutic target proteins. A full 80% of all lung cancers are of the non-small cell lung cancer (NSCLC) type and this general type can be broken down into 4 different subtypes based on histological analysis and these types are; adenocarcinoma, squamous cell carcinoma, bronchioalveolar carcinoma, and Large-cell undifferentiated carcinoma. The vast majority of NSCLC patients show subtypes of adenocarcinoma (ADC) or squamous cell carcinoma (SCC). Two recently-utilized targeted cancer therapies, pemetrexed and bevacizumab, have shown high success rates in treating NSCLC lung cancer but both drugs trigger a higher risk of bleeding in squamous cell carcinoma (SCC) patients. Thus their use is restricted to non-squamous, non-small cell lung cancer patients, most of whom are adenocarcinoma (ADC) patients, and an assay that can distinguish ADC from SCC would be highly valuable so that only those patients who would not be harmed and only benefit from treatment with these drugs are actually treated with these drugs. This embodiment provides peptides and peptide sequences for use in an SRM/MRM assay which will be useful for distinguishing adenocarcinoma (ADC) from squamous cell carcinoma (SCC) of the lung for improved treatment decisions for lung cancer therapy.

BRIEF DESCRIPTION OF THE DRAWINGS

FIG. 2 shows the expected changes in the pattern of expression of KRT7, NapsinA, TTF1, MUC1, KRT5, and TP63 in lung cancer samples for individual with adenocarcinoma and squamous cell carcinoma.

SUMMARY

Figure 1:
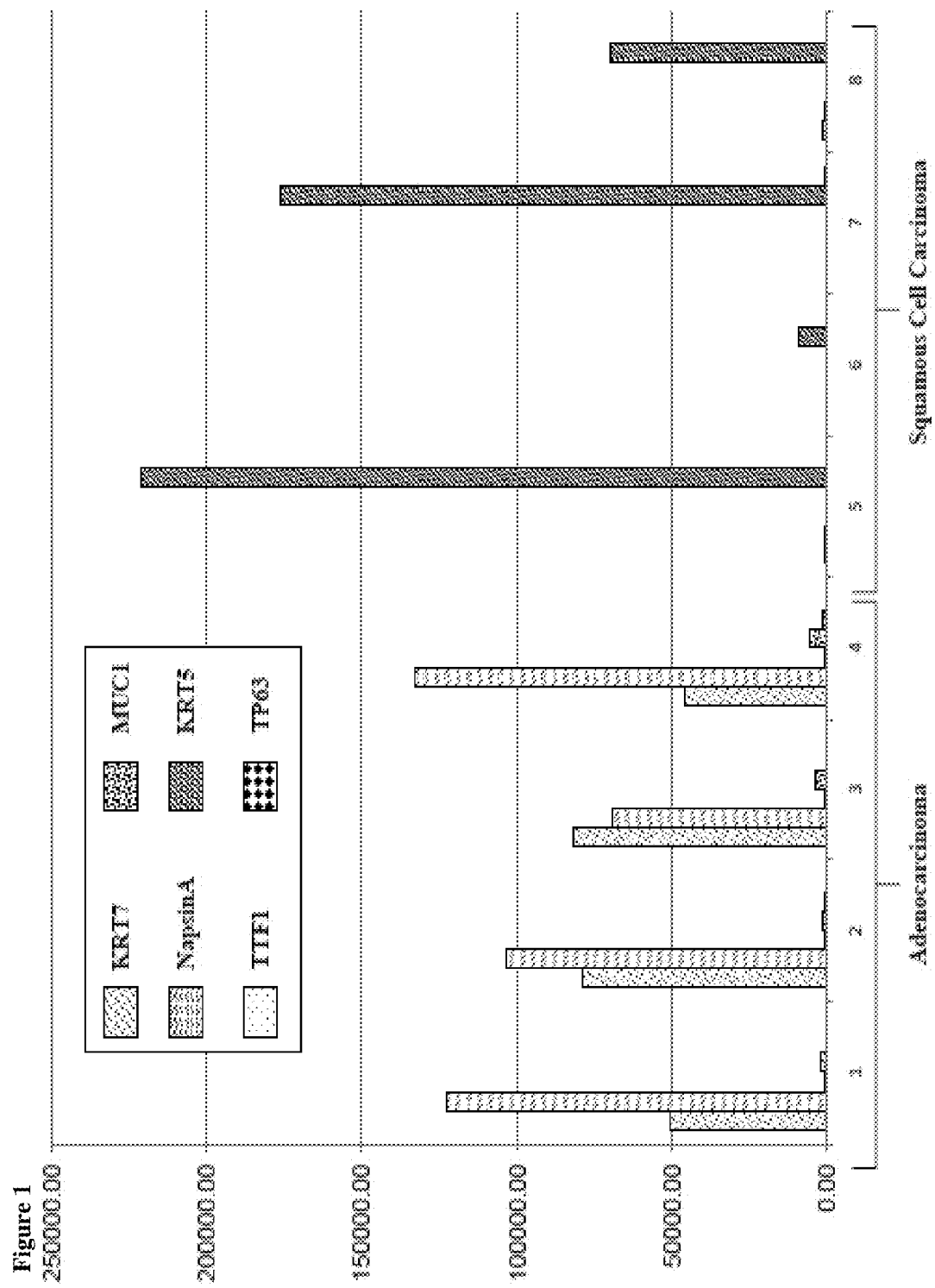
FIG. 1 shows a series of histograms indicating the level of KRT7, NapsinA, TTF1, MUC1, KRT5, and TP63 observed in eight formalin fixed lung tissue specimens obtained from human patients with adenocarcinoma or squamous cell carcinoma. Histograms one through four (1-4) show data obtained from tissue samples of patients with adenocarcinoma, and histograms five through eight (5-8) show data obtained from patients with squamous cell carcinoma. Each set of histograms shows, from left to right, the amount of KRT7, NapsinA, TTF1, MUC1, KRT5, and TP63 given in attomoles/microgram (amol/μg) of protein observed based on mass spectrometry analysis of tryptic peptides prepared using the Liquid Tissue protocol provided in U.S. Pat. No. 7,473,532. Numerical data are provided in the table that follows.

Specific peptides derived from subsequences of the following proteins are provided, Keratin 5 (KRT5 or KR5), Keratin 7 (KRT7 or KR7), NapsinA, thyroid transcription factor 1 (TTF1), tumor protein 63 (TP63), and mucin-1 (MUC1). Keratin 5 is also known as cytokeratin-5 and Type-II keratin Kb5 and will be referred to as KRT5. Keratin 7 is also known as cytokeratin-7 and will be referred to as KRT7. NapsinA is also known as Napsin-1, aspartyl protease 4, and ASP4, and will be referred to as NapsinA. Thyroid transcription factor 1 is also known as TITF1, TTF1, homeobox protein Nkx-2.1, homeobox protein NK-2 homolog A, and thyroid nuclear factor 1, and will be referred to as TTF1. Tumor protein 63 is also known as Keratinocyte transcription factor KET, Transformation-related protein 63, and chronic ulcerative stomatitis protein and will be referred to as TP63. Mucin-1 is also known as carcinoma-associated mucin, Episialin, CD227, and tumor-associated epithelial membrane antigen and will be referred to as MUC1.

The peptide sequence and fragmentation/transition ions for each peptide derived from proteins are potentially useful in a mass spectrometry-based Selected Reaction Monitoring (SRM) assay(s), which can also be referred to as a Multiple Reaction Monitoring (MRM) assay(s), hereinafter referred to as SRM/MRM assay(s). The use of peptides for SRM/MRM analysis of KRT5, KRT7, NapsinA, TTF1, TP63, and/or MUC1 proteins and isoforms of those proteins is described.

One or more, two or more, three or more, four or more, or five or six SRM/MRM assay(s) can be used to detect the presence and measure relative or absolute quantitative levels of one or more of the specific peptides from the KRT5, KRT7, NapsinA, TTF1, TP63, and/or MUC1 proteins, and therefore provide a means of measuring the total amount of each of those proteins in a given protein preparation obtained from a biological sample by mass spectrometry. All, or a portion of all of the available peptides from those proteins can also be analyzed simultaneously in a single SRM/MRM assay or can be analyzed in any combination of individual SRM/MRM assays. Each of the peptides provides a potential means of measuring the total amount of each of the corresponding proteins in a given protein preparation obtained from a biological sample by mass spectrometry.

The SRM/MRM assay(s) described herein can measure these peptides directly in complex protein lysate samples prepared from cells procured from patient tissue samples, such as formalin fixed cancer patient tissue (e.g., biopsies). Methods of preparing protein samples from formalin fixed tissue are described in U.S. Pat. No. 7,473,532, the contents of which are hereby incorporated by references in their entirety. The methods described in that patent may conveniently be carried out using Liquid Tissue reagents and protocol available from Expression Pathology Inc. (Rockville, Md.).

Formaldehyde/formalin fixation of tissues surgically removed from cancer patients is the accepted convention in pathology practice. As a result, formaldehyde/formalin fixed paraffin embedded tissue is the most widely available form of tissues from those patients. Formaldehyde/formalin fixation typically employs aqueous solutions of formaldehyde referred to as formalin. "100%" formalin consists of a saturated solution of formaldehyde (about 40% formaldehyde by volume or 37% by mass) in water, with a small amount of stabilizer, usually methanol to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay(s) can be used to correlate accurate and precise quantitative levels of any or all of these proteins, in addition to accurate and precise quantitative levels of potential isoforms of these proteins, within specific tissue samples (e.g., cancer tissue sample) of a patient or subject from whom the tissue (biological sample) was collected and preserved. This not only provides diagnostic information about the cancer, but also permits a physician or other medical professional to determine appropriate therapy for the patient or subject. Such an assay that provides diagnostically and therapeutically important information about levels of protein expression in a diseased tissue or in another patient/subject sample is termed a companion diagnostic assay. For example, such an assay can be designed to diagnose the stage, degree, or histology of a cancer and determine a therapeutic agent to which a patient or subject is most likely to respond.

More specifically, detection and/or quantitation of one or more, two or more, three or more, four or more, or five or more of the KRT7, MUC1, TTF1, and/or NapsinA proteins, and not the KRT5 and/or TP63 proteins, in cancer cells from a patient is indicative of a NSCLC being subtyped as ADC. The more of those proteins that are detected the higher the probability that the cancer is of the NSCLC Likewise, detection and quantitation of KRT5 and/or TP63 proteins, and not the KRT7, MUC1, TTF1, and/or NapsinA proteins, in cancer cells from a patient is indicative of a NSCLC being subtyped as SCC. While it has been found that many of the NSCLC patients can be subtyped using only the KRT5 and KRT7 proteins alone (ADC=KRT7>KRT5; SCC=KRT5>KRT7), the other proteins can be used to discriminate between ADC and SCC when either the KRT5 and/or KRT7 proteins are not detected and/or quantitated, and thus not useful for discriminating between ADC and SCC.

In the case when a patient's NSCLC is determined to be ADC by the detection and/or quantitation by expression of one, two, three, or more of the KRT7, MUC1, TTF1, and/or NapsinA proteins, then that patient's cancer may be treated with either pemetrexed and/or bevacizumab, which will not induce excessive and harmful bleeding in the patient. In the case where the patient's NSCLC is determined to be SCC by the detection and/or quantitation of one or both of the KRT5 and TP63 proteins, then that patient's cancer should not be treated with either pemetrexed and/or bevacizumab to avoid excessive and harmful bleeding of the patient.

DETAILED DESCRIPTION

The assays described herein quantify or measure relative or absolute levels of specific unmodified peptides from proteins including KRT5, KRT7, NapsinA, TTF1, TP63, and/or MUC1 and also can measure relative or absolute levels of specific modified peptides from those proteins. Examples of modifications include phosphorylated amino acid residues and glycosylated amino acid residues that are present on the peptides.

Relative quantitative levels of proteins and potential isoforms, can be determined by the SRM/MRM methodology, for example by comparing SRM/MRM signature peak areas (e.g., signature peak area or integrated fragment ion intensity). Relative levels of individual KRT5, KRT7, NapsinA, TTF1, TP63, and/or MUC1 peptides can be determined in different samples (e.g., a control sample and a sample prepared from a patient's or subject's tissue). Alternatively, where each peptide has its own specific SRM/MRM signature peak, it is possible to compare multiple SRM/MRM signature peak areas for one or more of KRT5, KRT7, NapsinA, TTF1, TP63, and/or MUC1 signature peptides. By comparing peak areas it is possible to determine the relative KRT5, KRT7, NapsinA, TTF1, TP63, and/or MUC1 protein and potential protein isoform content in one biological sample or in one or more additional or different biological samples. In this way, the relative amount of a particular peptide, or peptides, from the those proteins, and therefore the relative amount of the KRT5, KRT7, NapsinA, TTF1, TP63, and/or MUC1 proteins, and their potential isoforms, can be determined, across multiple (e.g., two, three, four, five, or more) biological samples under the same experimental conditions can be determined. In addition, relative quantitation can be determined for a given peptide, or peptides, from the KRT5, KRT7, NapsinA, TTF1, TP63, and/or MUC1 protein within a single sample by comparing the signature peak area for that peptide by SRM/MRM methodology to the signature peak area for another and different peptide, or peptides, from a different protein, or proteins, within the same protein preparation from the biological sample. Using such methodologies the amount of a particular peptide from the KRT5, KRT7, NapsinA, TTF1, TP63, and/or MUC1 protein, and therefore the amount of each of the corresponding proteins and their potential isoforms can be determined relative one to another within the same sample or in different samples. Since relative quantitation of an individual peptide, or peptides, may be conducted relative to the amount of another peptide, or peptides, within or between samples, it is possible to determine the relative amounts of the peptides present (e.g., by determining the peak area are relative one to another), regardless of the absolute weight to volume or weight to weight amounts of the proteins in the biological sample. Thus, the amounts of KRT5, KRT7, NapsinA, TTF1, TP63, and/or MUC1 peptide in the protein preparation from the biological sample may be used to determine the amounts of those proteins in and among various samples. Relative quantitative data about individual signature peak areas between different samples are generally normalized to the amount of protein analyzed per sample (e.g., the total protein concentration of a sample and the volume analyzed are used to normalize samples). Relative quantitation can be performed across many peptides from multiple proteins and the KRT5, KRT7, NapsinA, TTF1, TP63, and/or MUC1 protein(s) simultaneously in a single sample and/or across many samples to gain further insight into relative protein amounts, one peptide/protein with respect to other peptides/proteins.

Absolute quantitative levels of the KRT5, KRT7, NapsinA, TTF1, TP63, and/or MUC1 proteins are determined by, for example, the SRM/MRM methodology whereby the SRM/MRM signature peak area of an individual peptide from the KRT5, KRT7, NapsinA, TTF1, TP63, and/or MUC1 proteins in one biological sample is compared to the SRM/MRM signature peak area of a known amount of one or more internal standards "spiked" in the sample in known amounts (e.g., isotope labeled standards). In one embodiment, the internal standard is a synthetic version of the same exact KRT5, KRT7, NapsinA, TTF1, TP63, and/or MUC1 peptide that contains one or more amino acid residues labeled with one or more heavy isotopes. Such isotope labeled internal standards are synthesized so mass spectrometry analysis generates a predictable and consistent SRM/MRM signature peak that is different and distinct from the native KRT5, KRT7, NapsinA, TTF1, TP63, and/or MUC1 peptide signature peak and which can be used as a comparator peak. Thus, when the internal standard is spiked in known amounts into a protein or peptide preparation from a biological sample in known amounts and analyzed by mass spectrometry, the SRM/MRM signature peak area of the native peptide can be compared to the SRM/MRM signature peak area of the internal standard peptide. The numerical comparison permits a calculation of either the absolute molarity and/or absolute weight of the native peptide present in the original protein preparation from the biological sample, from which the concentration or weight of the corresponding protein may be determined. Absolute quantitative data for fragment peptides are typically displayed according to the amount of protein analyzed per sample. Absolute quantitation can be performed across many peptides, which permits a quantitative determination of multiple proteins (e.g., two, three, four, five, etc.) simultaneously in a single sample and/or across multiple samples to gain insight into absolute protein amounts in individual biological samples and/or in entire cohorts of individual samples. In one embodiment, the quantitation of proteins may be conducted using peptide standards as described by Gygi et al in U.S. Pat. No. 7,501,286.

As used herein the terms quantify, quantifying, measure or measuring mean to determine relative or absolute levels of an analyte, such as a protein, polypeptide, peptide, a standard (e.g., an internal standard).

In addition to being useful for distinguishing between ADC and SSC, the SRM/MRM assay methods described herein can be used as an aid for determining the stage of the cancer when employing, for example, patient-derived or subject-derived tissue, such as formalin fixed tissue. The SRM/MRM assays described herein may also be used as an aid in determining which therapeutic agent would be most advantageous for use in treating that patient or subject.

To examine the levels of the proteins associated with lung cancer described herein, analysis can be conducted on cancerous tissue or tissue that is suspected of being cancerous removed from a patient or subject, either through surgical removal of partial or entire tumors, or through biopsy procedures conducted to determine the presence or absence of suspected disease. Samples of the tissues are analyzed to determine whether or not one or more of KRT5, KRT7, NapsinA, TTF1, TP63, and/or MUC1 protein(s), and which forms of those proteins, are present in a patient's or subject's tissue. Moreover, the expression level of one or more of those proteins can be determined and compared to a "normal" or reference level found in healthy tissue. Normal or reference levels of proteins found in healthy tissue may be derived from, for example, the relevant tissues of one or more individuals that do not have cancer. Alternatively, normal or reference levels may be obtained for individuals with cancer by analysis of relevant tissues (e.g., portions of the same organ) not affected by the cancer.

Levels or amounts of proteins or peptides can be defined as the quantity expressed in moles, mass or weight of a protein or peptide determined by the SRM/MRM assay. The level or amount may be normalized to the total level or amount of protein or another component in the lysate analyzed (e.g., expressed in micromoles/microgram of protein or micrograms/microgram of protein) or even normalized to the amount of DNA on a per weight basis (e.g., micromoles or micrograms/microgram of DNA). In addition, the level or amount of a protein or peptide may be determined on volume basis, expressed, for example, in micromolar or nanograms/microliter. The level or amount of protein or peptide as determined by the SRM/MRM assay can also be normalized to the number of cells analyzed.

Information regarding KRT5, KRT7, NapsinA, TTF1, TP63, and/or MUC1 proteins, and isoforms of these proteins, can be used to aid in determining histological stage or grade of a cancer by correlating or comparing the level of the KRT5, KRT7, NapsinA, TTF1, TP63, and/or MUC1 proteins, and their isoforms, or fragment peptides with the levels observed in normal tissues. Once the histological stage and/or grade, and/or KRT5, KRT7, NapsinA, TTF1, TP63, and/or MUC1 protein-expression characteristics of the cancer has been determined, that information can be matched to a list of therapeutic agents (chemical and biological) developed to specifically treat cancer tissue that is characterized by, for example, abnormal expression of the protein or protein(s) (e.g., KRT5, KRT7, NapsinA, TTF1, TP63, and/or MUC1) that were assayed. Matching information from an KRT5, KRT7, NapsinA, TTF1, TP63, and/or MUC1 protein assay from a specific individual to a list of therapeutic agents that specifically targets cells/tissue expressing the KRT5, KRT7, NapsinA, TTF1, TP63, and/or MUC1 protein(s) represents a personalized medicine approach to treating lung cancers disease. The assay methods described herein form the foundation of a personalized medicine approach by using analysis of proteins from the patient's or subject's own tissue as a source for diagnostic and treatment decisions.

Peptide Generation

In principle, any predicted peptide derived from the KRT5, KRT7, NapsinA, TTF1, TP63, and/or MUC1 protein, prepared by any proteolytic process of known specificity may be used as a surrogate reporter to determine the abundance of KRT5, KRT7, NapsinA, TTF1, TP63, and/or MUC1 proteins. In one embodiment samples are digested with a protease or proteases of known specificity (e.g. one or more of trypsin, endoproteinase and/or Lys-C). One or more peptides resulting from the proteolytic treatment can be used as a surrogate reporter to determine the abundance of one or more of KRT5, KRT7, NapsinA, TTF1, TP63, and/or MUC1 proteins in a suitable assay such as a mass spectrometry-based SRM/MRM assay. Similarly, any predicted peptide sequence containing an amino acid residue at a site that is known to be modified in the KRT5, KRT7, NapsinA, TTF1, TP63, and/or MUC1 proteins may also be used to assay the extent of modification of KRT5, KRT7, NapsinA, TTF1, TP63, and/or MUC1 proteins in a sample.

KRT5, KRT7, NapsinA, TTF1, TP63, and/or MUC1 fragment peptides may be generated by a variety of means including by the use of the Liquid Tissue™ protocol provided in U.S. Pat. No. 7,473,532. The Liquid Tissue™ protocol and reagents are capable of producing peptide samples suitable for mass spectroscopic analysis from formalin fixed paraffin embedded tissue by proteolytic digestion of the proteins in the tissue/biological sample. In the Liquid Tissue™ protocol the tissue/biological is maintained at elevated temperatures in a buffer for an extended period of time (e.g., from about 80° C. to about 100° C. for a period of time from about 10 minutes to about 4 hours) to reverse or release protein cross-linking. The buffer employed is a neutral buffer, (e.g., a Tris-based buffer, or a buffer containing a detergent) and advantageously is a buffer that does not interfere with mass spectrometric analysis. Next, the tissue/biological sample is treated with one or more proteases, including but not limited to trypsin, chymotrypsin, pepsin, endoproteinase and Lys-C for a time sufficient to disrupt the tissue and cellular structure of said biological sample and to liquefy said sample (e.g., a period of time from about 30 minutes to about 24 hours at a temperature from about 37° C. to about 65° C.). The result of the heating and proteolysis is a liquid, soluble, dilutable biomolecule lysate. In one set of embodiment two or more proteases selected from trypsin, chymotrypsin, pepsin, endoproteinase, and Lys-C are employed in the proteolytic treatment of the biological sample.

Peptide Separation and Assay

Once lysates are prepared, peptides in the samples may be subject to a variety of techniques that facilitate their analysis and measurement (quantification). Where analysis is conducted by mass spectrometry, one or more chromatograph methods may be employed in order to facilitate the analysis.

In one embodiment the peptides are separated by liquid chromatography (LC) prior to analysis by a mass spectrometer instrument. For example, peptides can be separated on an nanoAcquityLC system (Waters, Milford, Mass.) or EASY-nLC II (Thermo Scientific, San Jose, Calif.) with a PicoFrit (100 μm ID/10 μm tip ID, New Objective) column self-packed to a bed length of 12 cm with Jupiter Proteo 90Å C12, 4 μm resin (Phenomenex, Torrance, Calif.). Peptides can be eluted over a 12 min chromatography gradient from 1% to 50% acetonitrile, containing 0.1% formic acid and at a flow rate of 800 nL/min Once separated by liquid chromatography, the eluted peptides are directed into a mass spectrometer for analysis. In one embodiment, mass spectrometer is equipped with a nanospray source.

In another embodiment, the peptides may be separated by an affinity technique, such as for example immunologically-based purification (e.g., immunoaffinity chromatography), chromatography on ion selective media, or if the peptides are modified, by separation using appropriate media such as lectins for separation of carbohydrate modified peptides. In still another embodiment, the SISCAPA method, which employs immunological separation of peptides prior to mass spectrometric analysis is employed. The SISCAPA technique is described, for example, in U.S. Pat. No. 7,632,686. In still other embodiments, lectin affinity methods (e.g., affinity purification and/or chromatography may be used to separate peptides from a lysate prior to analysis by mass spectrometry. Methods for separation of groups of peptides, including lectin-based methods, are described, for example, in Geng et al., J. Chromatography B, 752:293-306 (2001) Immunoaffinity chromatography techniques, lectin affinity techniques and other forms of affinity separation and/or chromatography (e.g., reverse phase, size based separation, ion exchange) may be used in any suitable combination to facilitate the analysis of peptides by mass spectrometry.

Surprisingly, it was found that many potential peptide sequences from the KRT5, KRT7, NapsinA, TTF1, TP63, and/or MUC1 proteins are unsuitable or ineffective for use in mass spectrometry-based SRM/MRM assays for reasons that are not evident. In particular it was found that many tryptic peptides from the KRT5, KRT7, NapsinA, TTF1, TP63, and/or MUC1 proteins could not be detected efficiently or at all in a Liquid Tissue™ lysate from formalin fixed, paraffin embedded tissue. As it was not possible to predict the most suitable peptides for MRM/SRM assay, it was necessary to experimentally identify modified and unmodified peptides in actual Liquid Tissue™ lysates to develop a reliable and accurate SRM/MRM assay for the KRT5, KRT7, NapsinA, TTF1, TP63, and/or MUC1 proteins. While not wishing to be bound by any theory, it is believed that some peptides might, for example, be difficult to detect by mass spectrometry as they do not ionize well or produce fragments distinct from other proteins, peptides may also fail to resolve well in separation (e.g., liquid chromatography), or adhere to glass or plastic ware. Accordingly, those peptides from the KRT5, KRT7, NapsinA, TTF1, TP63, and/or MUC1 proteins that can be detected in a Liquid Tissue™ lysate (e.g., the peptides in Tables 1 and 2) prepared from a formalin fixed tissue sample are the peptides for which SRM/MRM assays can be employed in a KRT5, KRT7, NapsinA, TTF1, TP63, and/or MUC1 proteins SRM/MRM assay. In one embodiment the protease employed in the simultaneous preparation of fragments of the KRT5, KRT7, NapsinA, TTF1, TP63, and/or MUC1 proteins in a single sample will be trypsin.

KRT5, KRT7, NapsinA, TTF1, TP63, and/or MUC1 peptides found in various embodiments described herein (e.g., Tables 1 and/or 2) were derived from the KRT5, KRT7, NapsinA, TTF1, TP63, and/or MUC1 proteins by trypsin digestion of all the proteins within a complex Liquid Tissue™ lysate prepared from cells procured from formalin fixed cancer tissue. Unless noted otherwise, in each instance the protease was trypsin. The Liquid Tissue™ lysate was then analyzed by mass spectrometry to determine those peptides derived from the KRT5, KRT7, NapsinA, TTF1, TP63, and/or MUC1 proteins that are detected and analyzed by mass spectrometry. Identification of a specific preferred subset of peptides for mass-spectrometric analysis is based on; 1) experimental determination of which peptide or peptides from a protein ionize in mass spectrometry analyses of Liquid Tissue™ lysates, and 2) the ability of the peptide to survive the protocol and experimental conditions used in preparing a Liquid Tissue™ lysate. This latter property extends not only to the amino acid sequence of the peptide but also to the ability of a modified amino acid residue within a peptide to survive in modified form during the sample preparation.

Protein lysates from cells procured directly from formalin (formaldehyde) fixed tissue were prepared using the Liquid Tissue™ reagents and protocol that entails collecting cells into a sample tube via tissue microdissection followed by heating the cells in the Liquid Tissue™ buffer for an extended period of time. Once the formalin-induced cross linking has been negatively affected, the tissue/cells are then digested to completion in a predictable manner using a protease, as for example including but not limited to the protease trypsin. Each protein lysate is turned into a collection of peptides by digestion of intact polypeptides with the protease. Each Liquid Tissue™ lysate was analyzed (e.g., by ion trap mass spectrometry) to perform multiple global proteomic surveys of the peptides where the data was presented as identification of as many peptides as could be identified by mass spectrometry from all cellular proteins present in each protein lysate. An ion trap mass spectrometer, or another form of a mass spectrometer that is capable of performing global profiling, for identification of as many peptides as possible from a single complex protein/peptide lysate is typically employed for analysis. Although SRM/MRM assay can be developed and performed on any type of mass spectrometer, including a MALDI, ion trap, or triple quadrupole, the most advantageous instrument platform for SRM/MRM assay is often considered to be a triple quadrupole instrument platform.

Once as many peptides as possible were identified in a single MS analysis of a single lysate under the conditions employed, then that list of peptides was collated and used to determine the proteins that were detected in that lysate. That process was repeated for multiple Liquid Tissue™ lysates, and the very large list of peptides was collated into a single dataset. That type of dataset can be considered to represent the peptides that can be detected in the type of biological sample that was analyzed (after protease digestion), and specifically in a Liquid Tissue™ lysate of the biological sample, and thus includes the peptides for specific proteins, such as for example the KRT5, KRT7, NapsinA, TTF1, TP63, and/or MUC1 proteins.

In one embodiment, the KRT5, KRT7, NapsinA, TTF1, TP63, and/or MUC1 tryptic peptides identified as useful in the determination of absolute or relative amounts of KRT5 (e.g., NCBI Accession No.: P13647, SEQ ID NO: 12), KRT7 (e.g., NCBI Accession No.: P08729, SEQ ID NO: 13), NapsinA (e.g., NCBI Accession No.: O96009, SEQ ID NO: 14), MUC1 (e.g., NCBI Accession No.: P15941, SEQ ID NO: 15), TTF1 (e.g., NCBI Accession No.: P43699, SEQ ID NO: 16), and/or TP63 (e.g., NCBI Accession No.: Q9H3D4, SEQ ID NO: 17), include one or more, two or more, three or more, four or more, five or more, six or more, seven or more, eight or more, nine or more, or ten or more or all of the peptides of SEQ ID NO:1, SEQ ID NO:2, SEQ ID NO:3, SEQ ID NO:4, SEQ ID NO:5, SEQ ID NO:6, SEQ ID NO:7, SEQ ID NO:8 SEQ ID NO:9, SEQ ID NO:10, and SEQ ID NO:11 each of which are listed in Table 1. Each of those peptides was detected by mass spectrometry in Liquid Tissue™ lysates prepared from formalin fixed, paraffin embedded tissue. Thus, each of the peptides in Table 1, or any combination of those peptides (e.g., one or more, two or more, three or more, four or more, five or more, six or more, or seven or more, eight or more, nine or more, or ten or more of those peptides recited in Table 1) are candidates for use in quantitative SRM/MRM assay for the KRT5, KRT7, NapsinA, TTF1, TP63, and/or MUC1 proteins including directly in formalin fixed patient or subject tissue.

TABLE 1

| SEQ ID | Protein | Peptide Sequence |
|---|---|---|
| SEQ ID NO: 1 | KRT5 | AQYEEIANR |
| SEQ ID NO: 2 | KRT5 | ISISTSGGSFR |
| SEQ ID NO: 3 | KRT7 | LPDIFEAQIAGLR |
| SEQ ID NO: 4 | KRT7 | SLDLDGIIAEVK |
| SEQ ID NO: 5 | NapsinA | FAIQYGTGR |
| SEQ ID NO: 6 | MUC1 | QGGFLGLSNIK |
| SEQ ID NO: 7 | MUC1 | SSVPSSTEK |
| SEQ ID NO: 8 | TTF1 | FPAISR |
| SEQ ID NO: 9 | TTF1 | VAVPVLVK |
| SEQ ID NO: 10 | TP63 | IPEQFR |
| SEQ ID NO: 11 | TP63 | TPSSASTVSVGSSETR |

The KRT5, KRT7, NapsinA, TTF1, TP63, and MUC1 peptides listed in Table 1 include those detected from multiple Liquid Tissue™ lysates of multiple different formalin fixed tissues of different human organs including prostate, colon, and breast. Each of those peptides is considered useful for quantitative SRM/MRM assay of the KRT5, KRT7, NapsinA, TTF1, TP63, and/or MUC1 proteins in formalin fixed tissue. Further data analysis of these experiments indicated no preference is observed for any specific peptides from any specific organ site. Thus, each of these peptides is believed to be suitable for conducting SRM/MRM assays of the KRT5, KRT7, NapsinA, TTF1, TP63, and/or MUC1 proteins on a Liquid Tissue™ lysate from any formalin fixed tissue originating from any biological sample or from any organ site in the body.

In another embodiment, an SRM/MRM assay employs one or two peptides for each of KRT5 and TP63 (e.g., from the peptides listed in Table 1). In another embodiment an SRM/MRM assay employs one or two peptides for each of KRT7, MUC1, TTF1, and NapsinA (e.g., from the peptides listed in Table 1).

In other embodiments one or both of KRT5 and TP63 proteins are assayed and one, two three or four of the KRT7, MUC1, TTF1, and NapsinA protein are assayed using SRM/MRM assay(s). In one example of such an embodiment, at least one or at least two peptide for one or both of the KRT5 and TP63 protein are assayed by SRM/MRM assay (e.g., the KRT5 and TP63 peptides listed in Table 1); and at least one or at least two peptides for any one, two, three or four of KRT7, MUC1, TTF1, and NapsinA are assayed (e.g., the peptides listed in Table 1). In another example of such an embodiment: at least one or at least two peptides for one or both of the KRT5 and TP63 protein are assayed by SRM/MRM assay (e.g., peptides listed in Table 1); and at least one or at least two peptides for any of KRT7, MUC1, TTF1, and NapsinA are assayed (e.g., the peptides listed in Table 1). Compositions comprising peptides that are isotopically labeled, but otherwise identical to one or more of the peptides set forth in any of these embodiments are provided for herein and their preparation use, particularly for use as mass spectrometry standards, is described below.

In one embodiment one or more peptides in Table 1, or any combination of those peptides (e.g., one or more, two or more, three or more, four or more, five or more, six or more, seven or more, eight or more, nine or more, or all eleven) is assayed by a method that does not rely upon mass spectroscopy, including, but not limited to, immunological methods (e.g., Western blotting or ELISA). In one embodiment, the assays are conducted using formalin fixed tissue. Regardless of how information directed to the amount of the peptide(s) (absolute or relative) is obtained, the information may be employed in any of the methods described herein, including indicating (diagnosing) the presence of cancer in a patient or subject, determining the stage/grade/status of the cancer, providing a prognosis, or determining the therapeutics or treatment regimen for a patient or subject.

In other embodiments one or both of KRT5 and TP63 proteins are assayed and one, two three or four of the KRT7, MUC1, TTF1, and NapsinA protein are assayed by a method that does not rely upon mass spectroscopy, including, but not limited to, immunological methods (e.g., Western blotting or ELISA). In one example of such an embodiment: at least one or at least two peptide for one or both of the KRT5 and TP63 protein are assayed (e.g., the KRT5 and TP63 peptides listed in Table 1); and at least one or at least two peptides for any one, two, three or four of KRT7, MUC1, TTF1, and NapsinA are assayed (e.g., the peptides listed in Table 1). In another example of such an embodiment: at least one or at least two peptides for one or both of the KRT5 and TP63 protein are (e.g., the KRT5 and TP63 peptides listed in Table 1); and at least one or at least two peptides for any of KRT7, MUC1, TTF1, and NapsinA are assayed (e.g., the peptides listed in Table 1).

An important consideration when conducting an SRM/MRM assay is the type of instrument that may be employed in the analysis of the peptides. Although SRM/MRM assays can be developed and performed on any type of mass spectrometer, including a MALDI, ion trap, or triple quadrupole, presently the most advantageous instrument platform for SRM/MRM assay is often considered to be a triple quadrupole instrument platform. That type of a mass spectrometer may be considered to be the most suitable instrument for analyzing a single isolated target peptide within a very complex protein lysate that may consist of hundreds of thousands to millions of individual peptides from all the proteins contained within a cell.

In order to most efficiently implement a SRM/MRM assay for each peptide derived from the KRT5, KRT7, NapsinA, TTF1, TP63, and/or MUC1 proteins it is desirable to utilize information in addition to the peptide sequence in the analysis. That additional information may be used in directing and instructing the mass spectrometer (e.g. a triple quadrupole mass spectrometer) to perform the correct and focused analysis of specific targeted peptide(s) such that the assay may be effectively performed.

The additional information about target peptides in general, and about specific KRT5, KRT7, NapsinA, TTF1, TP63, and MUC1 peptides, may include one, two, three, four, or more of the mono isotopic mass of each peptide, its precursor charge state, the precursor m/z value, the m/z transition ions, and the ion type of each transition ion. Additional peptide information that may be used to develop an SRM/MRM assay for the KRT5, KRT7, NapsinA, TTF1, TP63, and/or MUC1 proteins is shown in Table 2 for all eleven (11) KRT5, KRT7, NapsinA, TTF1, TP63, and MUC1 peptides from the list in Table 1. This additional information described for the peptides as shown in Table 2 may be prepared, obtained, and applied to the analysis of any other peptides from the KRT5, KRT7, NapsinA, TTF1, TP63, and/or MUC1 proteins, including those produced by the action of other proteases or combinations of proteases (e.g., trypsin and/or Lys C).

TABLE 2

| SEQ ID | Protein | Peptide Sequence | Mono Isotopic Mass | Precursor Charge State | Precursor m/z | Product Transition m/z | Ion Type |
|---|---|---|---|---|---|---|---|
| SEQ ID NO: 1 | KRT5 | AQYEEIANR | 1092.52 | 2 | 547.267 | 602.325 | y5 |
| | | | | 2 | | 731.368 | y6 |
| | | | | 2 | | 894.431 | y7 |
| SEQ ID NO: 2 | KRT5 | ISISTSGGSFR | 1110.57 | 2 | 556.291 | 610.294 | y6 |
| | | | | 2 | | 711.342 | y7 |
| | | | | 2 | | 798.374 | y8 |
| SEQ ID NO: 3 | KRT7 | LPDIFEAQIAGLR | 1441.79 | 2 | 721.904 | 728.441 | y7 |
| | | | | 2 | | 857.483 | y8 |
| | | | | 2 | | 1004.552 | y9 |
| SEQ ID NO: 4 | KRT7 | SLDLDGIIAEVK | 1271.7 | 2 | 636.856 | 729.45 | y7 |
| | | | | 2 | | 844.477 | y8 |
| | | | | 2 | | 1072.588 | y10 |
| SEQ ID NO: 5 | NapsinA | FAIQYGTGR | 1011.51 | 2 | 506.764 | 553.272 | y5 |
| | | | | 2 | | 681.331 | y6 |
| | | | | 2 | | 794.415 | y7 |
| SEQ ID NO: 6 | MUC1 | QGGFLGLSNIK | 1132.62 | 2 | 567.319 | 574.355 | y5 |
| | | | | 2 | | 631.377 | y6 |
| | | | | 2 | | 744.461 | y7 |
| SEQ ID NO: 7 | MUC1 | SSVPSSTEK | 920.445 | 2 | 461.23 | 551.267 | y5 |
| | | | | 2 | | 648.319 | y6 |
| | | | | 2 | | 747.388 | y7 |
| SEQ ID NO: 8 | TTF1 | FPAISR | 689.386 | 2 | 345.7 | 375.235 | y3 |
| | | | | 2 | | 446.272 | y4 |
| | | | | 2 | | 543.324 | y5 |
| SEQ ID NO: 9 | TTF1 | VAVPVLVK | 823.553 | 2 | 412.784 | 555.386 | y5 |
| | | | | 2 | | 654.454 | y6 |
| | | | | 2 | | 725.492 | y7 |
| SEQ ID NO: 10 | TP63 | IPEQFR | 788.418 | 2 | 395.216 | 450.245 | y3 |
| | | | | 2 | | 579.288 | y4 |
| | | | | 2 | | 676.341 | y5 |
| SEQ ID NO: 11 | TP63 | TPSSASTVSVGSSETR | 1551.74 | 2 | 776.876 | 822.395 | y8 |
| | | | | 2 | | 921.463 | y9 |
| | | | | 2 | | 1109.543 | y11 |

In some embodiments, the peptides suitable for assays of KRT5, KRT7, NapsinA, TTF1, TP63, and/or MUC1 proteins (e.g., the peptides set forth in SEQ, ID, Nos 1-11) may contain additional proteolytic sites internal to the peptide sequences that if cleaved would produce sub-peptides. Such sub-peptides are recognizable by assessing the sequence of the identified peptides for proteolytic cleavage sites of a desired protease. In one embodiment, tryptic peptides may include additional internal trypsin cleavage sites that can lead to sub-peptides upon further cleavage by trypsin. In another embodiment, tryptic peptides may contain internal sites for proteases including, but not limited to, trypsin GluC, AspN, chymotrypsin, and/or Lys C, which can lead to the formation of sub-peptides upon cleavage by any one, two, or more of trypsin, GluC, AspN, chymotrypsin, and/or Lys C. In another embodiment, Lys C peptides may contain internal sites for other proteases, such as GluC, AspN, chymotrypsin, and/or trypsin, which can lead to the formation of sub-peptides upon cleavage by any one, two, or more of GluC, AspN, chymotrypsin, and/or trypsin. Such sub-peptides, and specifically trypsin, GluC, AspN, chymotrypsin, and/or Lys C cleavage fragments of any one or more of the peptides set forth in SEQ ID Nos.: 1-11 are understood to be set forth and within the scope of this disclosure.

Embodiments set forth herein include compositions comprising one or more of the peptides in Tables 1 and 2, and may optionally include peptides that are isotopically labeled but otherwise identical to one or more of the peptides found in Tables 1 and 2. In some embodiments, the compositions comprise one or more, two or more, three or more, four or more, five or more, six or more, seven or more, eight or more, nine or more, or all eleven of the peptides in Tables 1 and 2. Such compositions may optionally include peptides, polypeptides, or proteins whose amino acid sequence comprises peptides that are isotopically labeled but otherwise identical to one or more of the peptides found in Table 1 and Table 2. Where isotopically labeled synthetic or natural peptides, polypeptides, or proteins that comprise one, two, three, four, five, six or more of the peptides in Tables 1 and 2 are employed, protease treatment releases peptides that are isotopically labeled but otherwise identical to the peptides in Tables 1 and 2. Such isotopically labeled biological or biosynthetic peptides may be prepared, for example, in programmed cell lysates or in tissue culture using isotopically labeled amino acids. Each of the isotopically labeled peptides may be labeled with one or more isotopes selected independently from the group consisting of: $^{18}O$, $^{17}O$, $^{34}S$, $^{15}N$, $^{13}C$, $^{2}H$ or combinations thereof. Compositions comprising peptides from the KRT5, KRT7, NapsinA, TTF1, TP63, and/or MUC1 proteins, whether isotope labeled or not, do not need to contain all of the peptides from that protein (e.g., a complete set of tryptic peptides). In some embodiments the compositions do not contain all peptides in combination from KRT5, KRT7, NapsinA, TTF1, TP63, and/or MUC1 proteins, and particularly all of the peptides appearing in Table 1 and Table 2. Compositions comprising peptides may be in the form of dried or lyophilized materials, liquid (e.g., aqueous) solutions or suspensions, arrays, or blots.

In one embodiment, the additional information about specific KRT5, KRT7, NapsinA, TTF1, TP63, and MUC1 peptides, includes one or more, two or more, or three or more of the mono isotopic mass of each peptide, its precursor charge state, the precursor m/z value, the m/z transition ions, and the ion type of each transition ion for peptides resulting from Lys C proteolysis of KRT5, KRT7, NapsinA, TTF1, TP63, and/or MUC1 proteins.

In another embodiment, the additional information about specific KRT5, KRT7, NapsinA, TTF1, TP63, and MUC1 peptides, includes one or more, two or more, or three or more of the mono isotopic mass of each peptide, its precursor charge state, the precursor m/z value, the m/z transition ions, and the ion type of each transition ion for peptides resulting from trypsin proteolysis of KRT5, KRT7, NapsinA, TTF1, TP63, and/or MUC1 proteins.

In still another embodiment, the additional information about specific KRT5, KRT7, NapsinA, TTF1, TP63, and MUC1 peptides, includes one or more, two or more, or three or more of the mono isotopic mass of each peptide, its precursor charge state, the precursor m/z value, the m/z transition ions, and the ion type of each transition ion for peptides resulting from trypsin and/or Lys C proteolysis of KRT5, KRT7, NapsinA, TTF1, TP63, and/or MUC1 proteins. In one embodiment, a single tryptic and/or Lys C proteolytic peptide from each of the KRT5, KRT7, NapsinA, TTF1, TP63, and/or MUC1, along with the relevant additional information is employed in a diagnostic determination. Thus, for example, the peptides of SEQ ID NOs 2, 3, 5, 6, 8 and/or 11, and additional information about those peptides (see Table 3) is employed in a diagnostic analysis.

TABLE 3

| SEQ ID | Protein | Peptide Sequence | Mono Isotopic Mass | Precursor Charge State | Precursor m/z | Product Transition m/z | Ion Type |
|---|---|---|---|---|---|---|---|
| SEQ ID NO: 2 | KRT5 | ISISTSGGSFR | 1110.57 | 2 | 556.291 | 610.294 | y6 |
| | | | | 2 | | 711.342 | y7 |
| | | | | 2 | | 798.374 | y8 |
| SEQ ID NO: 3 | KRT7 | LPDIFEAQIAGLR | 1441.79 | 2 | 721.904 | 728.441 | y7 |
| | | | | 2 | | 857.483 | y8 |
| | | | | 2 | | 1004.552 | y9 |
| SEQ ID NO: 5 | NapsinA | FAIQYGTGR | 1011.51 | 2 | 506.764 | 553.272 | y5 |
| | | | | 2 | | 681.331 | y6 |
| | | | | 2 | | 794.415 | y7 |
| SEQ ID NO: 6 | MUC1 | QGGFLGLSNIK | 1132.62 | 2 | 567.319 | 574.355 | y5 |
| | | | | 2 | | 631.377 | y6 |
| | | | | 2 | | 744.461 | y7 |

TABLE 3-continued

| SEQ ID | Protein | Peptide Sequence | Mono Isotopic Mass | Precursor Charge State | Precursor m/z | Product Transition m/z | Ion Type |
|---|---|---|---|---|---|---|---|
| SEQ ID NO: 8 | TTF1 | FPAISR | 689.386 | 2 | 345.7 | 375.235 | y3 |
| | | | | 2 | | 446.272 | y4 |
| | | | | 2 | | 543.324 | y5 |
| SEQ ID NO: 11 | TP63 | TPSSASTVSVGSSETR | 1551.74 | 2 | 776.876 | 822.395 | y8 |
| | | | | 2 | | 921.463 | y9 |
| | | | | 2 | | 1109.543 | y11 |

Certain Embodiments

Certain embodiments of the invention are described below.

1. A method for measuring the level of the KRT5, KRT7, NapsinA, TTF1, TP63, and/or MUC1 proteins in a biological sample, comprising detecting and/or quantifying the amount of one or more modified and/or unmodified KRT5, KRT7, NapsinA, TTF1, TP63, and/or MUC1 protein fragment peptides in a protein digest prepared from said biological sample using mass spectrometry; and calculating the level of modified or unmodified KRT5, KRT7, NapsinA, TTF1, TP63, and/or MUC1 protein in said sample; and
wherein said amount is a relative amount or an absolute amount.

2. The method of embodiment 1, further comprising the step of fractionating said protein digest prior to detecting and/or quantifying the amount of one or more modified or unmodified KRT5, KRT7, NapsinA, TTF1, TP63, and/or MUC1 protein fragment peptides.

3. The method of embodiment 2, wherein said fractionating step is selected from the group consisting of gel electrophoresis, liquid chromatography, capillary electrophoresis, nano-reversed phase liquid chromatography, high performance liquid chromatography, or reverse phase high performance liquid chromatography.

4. The method of any of embodiments 1-3, wherein said protein digest of said biological sample is prepared by the Liquid Tissue™ protocol.

5. The method of any of embodiments 1-3, wherein said protein digest comprises a protease digest.

6. The method of embodiment 5, wherein said protein digest comprises a trypsin and/or lys C digest.

7. The method of any of embodiments 1-6, wherein said mass spectrometry comprises tandem mass spectrometry, ion trap mass spectrometry, triple quadrupole mass spectrometry, MALDI-TOF mass spectrometry, MALDI mass spectrometry, and/or time of flight mass spectrometry.

8. The method of embodiment 7, wherein the mode of mass spectrometry used is Selected Reaction Monitoring (SRM), Multiple Reaction Monitoring (MRM), and/or multiple Selected Reaction Monitoring (mSRM), or any combination thereof.

9. The method of any of embodiments 1 to 8, wherein the KRT5, KRT7, NapsinA, TTF1, TP63, and/or MUC1 protein fragment peptides comprises an amino acid sequence as set forth as SEQ ID NO:1, SEQ ID NO:2, SEQ ID NO:3, SEQ ID NO:4, SEQ ID NO:5, SEQ ID NO:6, SEQ ID NO:7, SEQ ID NO:8 SEQ ID NO:9, SEQ ID NO:10, and/or SEQ ID NO:11.

10. The method of any of embodiments 1-9, wherein the biological sample is a blood sample, a urine sample, a serum sample, an ascites sample, a sputum sample, lymphatic fluid, a saliva sample, a cell, or a solid tissue.

11. The method of any of embodiments 1-10, wherein the biological sample is formalin fixed tissue.

12. The method of any of embodiments 1-11, wherein the biological sample is paraffin embedded tissue.

13. The method of any of embodiments 1-12, wherein the biological sample is tissue that is obtained from a tumor.

14. The method of embodiment 13, wherein the tumor is a primary tumor.

15. The method of embodiment 13, wherein the tumor is a secondary tumor.

16. The method of any of embodiments 1 to 15, further comprising quantifying modified and/or unmodified KRT5, KRT7, NapsinA, TTF1, TP63, and/or MUC1 protein fragment peptides.

17(a). The method of any of embodiments 1-16, wherein quantifying the KRT5, KRT7, NapsinA, TTF1, TP63, and/or MUC1 protein fragment peptides comprises comparing an amount of one or more KRT5, KRT7, NapsinA, TTF1, TP63, and MUC1 protein fragment peptides comprising an amino acid sequence of about 8 to about 45 amino acid residues of KRT5, KRT7, NapsinA, TTF1, TP63, and/or MUC1 proteins in one biological sample to the amount of the same KRT5, KRT7, NapsinA, TTF1, TP63, and/or MUC1 protein fragment peptides in a different and separate sample or biological sample.

17(b). The method of any of embodiments 1-16, wherein quantifying the KRT5, KRT7, NapsinA, TTF1, TP63, and/or MUC1 protein fragment peptides comprises comparing an amount of one or more KRT5, KRT7, NapsinA, TTF1, TP63, and MUC1 protein fragment peptides comprising an amino acid sequence of about 8 to about 45 amino acid residues of KRT5, KRT7, NapsinA, TTF1, TP63, and/or MUC1 proteins, as shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8 SEQ ID NO:9, SEQ ID NO:10, and SEQ ID NO:11, in one biological sample to the amount of the same KRT5, KRT7, NapsinA, TTF1, TP63, and/or MUC1 protein fragment peptides in a different and separate biological sample.

18. The method of embodiment 17(a) or 17(b), wherein quantifying one or more KRT5, KRT7, NapsinA, TTF1, TP63, and/or MUC1 protein fragment peptides comprises determining the amount of the each of the KRT5, KRT7, NapsinA, TTF1, TP63, and/or MUC1 protein fragment peptides in a biological sample by comparison to an added internal standard peptide of known amount, wherein each of the KRT5, KRT7, NapsinA, TTF1, TP63, and/or MUC1 protein fragment peptides in the biological sample is compared to an added internal standard peptide having the same amino acid sequence.

19. The method of embodiment 18, wherein the internal standard peptide is an isotopically labeled peptide.

20. The method of embodiment 19, wherein the isotopically labeled internal standard peptide comprises one or more heavy stable isotopes selected from $^{18}$O, $^{17}$O, $^{34}$S, $^{15}$N, $^{13}$C, $^{2}$H or combinations thereof.

21. The method of any of embodiments 1-20, wherein detecting and/or quantifying the amount of one or more modified or unmodified KRT5, KRT7, NapsinA, TTF1, TP63, and/or MUC1 protein fragment peptides in the protein digest indicates the presence of modified and/or unmodified KRT5, KRT7, NapsinA, TTF1, TP63, and/or MUC1 protein and an association with cancer (e.g., ADC and/or SSC) in a patient or subject.

22. The method of embodiment 21, further comprising correlating the results of said detecting and/or quantifying the amount of one or more modified and/or unmodified KRT5, KRT7, NapsinA, TTF1, TP63, and/or MUC1 protein fragment peptides, or the amount of said KRT5, KRT7, NapsinA, TTF1, TP63, and/or MUC1 proteins to the diagnostic stage/grade/status of the cancer.

23. The method of embodiment 22, wherein correlating the results of said detecting and/or quantifying the amount of one or more modified or unmodified KRT5, KRT7, NapsinA, TTF1, TP63, and/or MUC1 protein fragment peptides, or the amount of said KRT5, KRT7, NapsinA, TTF1, TP63, and/or MUC1 proteins to the diagnostic stage/grade/status of the cancer is combined with detecting and/or quantifying the amount of other proteins or peptides from other proteins in a multiplex format to provide additional information about the diagnostic stage/grade/status of the cancer.

24. The method of any one of embodiments 1-23, further comprising selecting for a patient or subject from which said biological sample was obtained a treatment based on the presence, absence, or amount of one or more KRT5, KRT7, NapsinA, TTF1, TP63, and/or MUC1 protein fragment peptides or the amount of KRT5, KRT7, NapsinA, TTF1, TP63, and/or MUC1 proteins.

25. The method of any one of embodiments 1-24, further comprising administering to a patient or subject from which said biological sample was obtained a therapeutically effective amount of a therapeutic agent, wherein the therapeutic agent and/or amount of the therapeutic agent administered is based upon amount of one or more modified or unmodified KRT5, KRT7, NapsinA, TTF1, TP63, and/or MUC1 protein fragment peptides or the amount of KRT5, KRT7, NapsinA, TTF1, TP63, and/or MUC1 proteins.

26. The method of embodiments 24 and 25, wherein the treatment or the therapeutic agent is directed to cancer cells expressing KRT5, KRT7, NapsinA, TTF1, TP63, and/or MUC1 proteins.

27. The method of embodiment 26, wherein said therapeutic is selected from pemetrexed and bevacizumab.

28. The method of embodiments 1-27, wherein the biological sample is formalin fixed tumor tissue that has been processed for quantifying the amount of one or more modified or unmodified KRT5, KRT7, NapsinA, TTF1, TP63, and/or MUC1 protein fragment peptides employing the Liquid Tissue™ protocol and reagents.

29. The method of any of embodiments 1-28, wherein said one or more modified or unmodified KRT5, KRT7, NapsinA, TTF1, TP63, and/or MUC1 protein fragment peptides is one or more of the peptides in Table 1.

30. A composition comprising one or more, two or more, three or more, four or more, five or more, six or more, seven or more, eight or more, nine or more, or ten or more of the peptides in Table 1 and/or antibodies thereto.

31. The composition of embodiment 30, comprising one or more, two or more, three or more, four or more, five or more, six or more, seven or more, eight or more, nine or more, or ten or more of the peptides of Table 2 or antibodies thereto Exemplary SRM/MRM Assay Method 1. The method described below was used to: 1) identify candidate peptides from the KRT5, KRT7, NapsinA, TTF1, TP63, and/or MUC1 proteins that can be used for a mass spectrometry-based SRM/MRM assay for the KRT5, KRT7, NapsinA, TTF1, TP63, and/or MUC1 proteins, 2) develop individual SRM/MRM assay, or assays, for target peptides from the KRT5, KRT7, NapsinA, TTF1, TP63, and/or MUC1 proteins, and 3) apply quantitative assays to cancer diagnosis and/or choice of optimal therapy. Identification of SRM/MRM candidate fragment peptides for the KRT5, KRT7, NapsinA, TTF1, TP63, and/or MUC1 proteins a. Prepare a Liquid Tissue™ protein lysate from a formalin fixed biological sample using a protease or proteases, (that may or may not include trypsin), to digest proteins b. Analyze all protein fragments in the Liquid Tissue™ lysate on an ion trap tandem mass spectrometer and identify all fragment peptides from the KRT5, KRT7, NapsinA, TTF1, TP63, and/or MUC1 proteins, where individual fragment peptides do not contain any peptide modifications such as phosphorylations or glycosylations c. Analyze all protein fragments in the Liquid Tissue™ lysate on an ion trap tandem mass spectrometer and identify all fragment peptides from the KRT5, KRT7, NapsinA, TTF1, TP63, and/or MUC1 proteins that carry peptide modifications such as for example phosphorylated or glycosylated residues d. All peptides generated by a specific digestion method from the entire, full length KRT5, KRT7, NapsinA, TTF1, TP63, and/or MUC1 proteins potentially can be measured, but preferred peptides used for development of the SRM/MRM assay are those that are identified by mass spectrometry directly in a complex Liquid Tissue™ protein lysate prepared from a formalin fixed biological sample e. Peptides that are specifically modified (phosphorylated, glycosylated, etc.) in a patient or subject tissue and which ionize, and thus can be detected, in a mass spectrometer when analyzing a Liquid Tissue™ lysate from a formalin fixed biological sample are identified as candidate peptides for assaying peptide modifications of the KRT5, KRT7, NapsinA, TTF1, TP63, and/or MUC1 proteins 2. Mass Spectrometry Assay for Fragment Peptides from KRT5, KRT7, NapsinA, TTF1, TP63, and/or MUC1 proteins a. SRM/MRM assay on a triple quadrupole mass spectrometer for individual fragment peptides identified in a Liquid Tissue™ lysate is applied to peptides from the KRT5, KRT7, NapsinA, TTF1, TP63, and/or MUC1 proteins i. Determine optimal retention time for a fragment peptide for optimal chromatography conditions including but not limited to gel electrophoresis, liquid chromatography, capillary electrophoresis, nano-reversed phase liquid chromatography, high performance liquid chromatography, or reverse phase high performance liquid chromatography ii. Determine the mono isotopic mass of the peptide, the precursor charge state for each peptide, the precursor m/z value for each peptide, the m/z transition ions for each peptide, and the ion type of each transition ion for each fragment peptide in order to develop an SRM/MRM assay for each peptide.
  iii. SRM/MRM assay can then be conducted using the information from (i) and (ii) on a triple quadrupole mass spectrometer where each peptide has a characteristic and unique SRM/MRM signature peak that precisely defines the unique SRM/MRM assay as performed on a triple quadrupole mass spectrometer
 b. Perform SRM/MRM analysis so that the amount of the fragment peptide of the KRT5, KRT7, NapsinA, TTF1, TP63, and/or MUC1 proteins that is detected, as a function of the unique SRM/MRM signature peak area from an SRM/MRM mass spectrometry analysis, can indicate both the relative and absolute amount of the KRT5, KRT7, NapsinA, TTF1, TP63, and/or MUC1 proteins in a particular protein lysate.
  i. Relative quantitation may be achieved by:
   1. Determining increased or decreased presence of the KRT5, KRT7, NapsinA, TTF1, TP63, and/or MUC1 proteins by comparing the SRM/MRM signature peak area from a given KRT5, KRT7, NapsinA, TTF1, TP63, and/or MUC1 peptide detected in a Liquid Tissue™ lysate from one formalin fixed biological sample to the same SRM/MRM signature peak area of the same KRT5, KRT7, NapsinA, TTF1, TP63, and/or MUC1 fragment peptide in at least a second, third, fourth or more Liquid Tissue™ lysates from least a second, third, fourth or more formalin fixed biological samples
   2. Determining increased or decreased presence of the KRT5, KRT7, NapsinA, TTF1, TP63, and/or MUC1 proteins by comparing the SRM/MRM signature peak area from a given KRT5, KRT7, NapsinA, TTF1, TP63, and MUC1 peptide detected in a Liquid Tissue™ lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.
   3. Determining increased or decreased presence of the KRT5, KRT7, NapsinA, TTF1, TP63, and/or MUC1 proteins by comparing the SRM/MRM signature peak area for a given KRT5, KRT7, NapsinA, TTF1, TP63, and MUC1 peptide to the SRM/MRM signature peak areas from other fragment peptides derived from different proteins within the same Liquid Tissue™ lysate from the formalin fixed biological sample in order to normalize changing levels of KRT5, KRT7, NapsinA, TTF1, TP63, and/or MUC1 proteins to levels of other proteins that do not change their levels of expression under various cellular conditions.
   4. These assays can be applied to both unmodified fragment peptides and for modified fragment peptides of the KRT5, KRT7, NapsinA, TTF1, TP63, and/or MUC1 proteins, where the modifications include but are not limited to phosphorylation and/or glycosylation, and where the relative levels of modified peptides are determined in the same manner as determining relative amounts of unmodified peptides.
  ii. Absolute quantitation of a given peptide may be achieved by comparing the SRM/MRM signature peak area for a given fragment peptide from the KRT5, KRT7, NapsinA, TTF1, TP63, and/or MUC1 proteins in an individual biological sample to the SRM/MRM signature peak area of an internal fragment peptide standard spiked into the protein lysate from the biological sample
   1. The internal standard is a labeled synthetic version of the fragment peptide from the KRT5, KRT7, NapsinA, TTF1, TP63, and/or MUC1 proteins that is being interrogated. This standard is spiked into a sample in known amounts, and the SRM/MRM signature peak area can be determined for both the internal fragment peptide standard and the native fragment peptide in the biological sample separately, followed by comparison of both peak areas
   2. This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.
 3. Apply Fragment Peptide Quantitation to Cancer Diagnosis and Treatment
  a. Perform relative and/or absolute quantitation of fragment peptide levels of the KRT5, KRT7, NapsinA, TTF1, TP63, and/or MUC1 proteins and demonstrate that the previously-determined association, as well understood in the field of cancer, of KRT5, KRT7, NapsinA, TTF1, TP63, and MUC1 protein expression to the stage/grade/status of cancer in patient or subject tumor tissue is confirmed
  b. Perform relative and/or absolute quantitation of fragment peptide levels of the KRT5, KRT7, NapsinA, TTF1, TP63, and/or MUC1 proteins and demonstrate correlation with clinical outcomes from different treatment strategies, wherein this correlation has already been demonstrated in the field or can be demonstrated in the future through correlation studies across cohorts of patients or subjects and tissue from those patients or subjects. Once either previously established correlations or correlations derived in the future are confirmed by this assay then the assay method can be used to determine optimal treatment strategy A Mass Spectrometry Assay for Fragment Peptides from KRT5, KRT7, NapsinA, TTF1, TP63, and/or MUC1 proteins
 a. SRM/MRM assay to determine the amount of the fragment peptide of the KRT5, KRT7, NapsinA, TTF1, TP63, and/or MUC1 proteins that is detected to determine the relative and/or absolute amount of the KRT5, KRT7, NapsinA, TTF1, TP63, and/or MUC1 proteins in a protein lysate.
  i. Relative quantitation may be achieved by:
   1. Determining increased or decreased presence of the KRT5, KRT7, NapsinA, TTF1, TP63, and/or MUC1 proteins by comparing the SRM/MRM signature peak area from a given KRT5, KRT7, NapsinA, TTF1, TP63, and MUC1 protein peptide detected in a Liquid Tissue™ lysate from one formalin fixed biological sample to the same SRM/MRM signature peak area of the same KRT5, KRT7, NapsinA, TTF1, TP63, and MUC1 protein fragment peptide in at least a second, third, fourth or more Liquid Tissue™ lysates from least a second, third, fourth or more formalin fixed biological samples 2. Determining increased or decreased presence of the KRT5, KRT7, NapsinA, TTF1, TP63, and/or MUC1 proteins by comparing the SRM/MRM signature peak area from a given KRT5, KRT7, NapsinA, TTF1, TP63, and MUC1 protein peptide detected in a Liquid Tissue™ lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.

3. Determining increased or decreased presence of the KRT5, KRT7, NapsinA, TTF1, TP63, and/or MUC1 proteins by comparing the SRM/MRM signature peak area for a given KRT5, KRT7, NapsinA, TTF1, TP63, and MUC1 protein peptide to the SRM/MRM signature peak areas from other fragment peptides derived from different proteins within the same Liquid Tissue™ lysate from the formalin fixed biological sample in order to normalize changing levels of KRT5, KRT7, NapsinA, TTF1, TP63, and/or MUC1 proteins to levels of other proteins that do not change their levels of expression under various cellular conditions.

4. These assays can be applied to both unmodified fragment peptides and for modified fragment peptides of the KRT5, KRT7, NapsinA, TTF1, TP63, and/or MUC1 proteins, where the modifications include but are not limited to phosphorylation and/or glycosylation, and where the relative levels of modified peptides are determined in the same manner as determining relative amounts of unmodified peptides.

ii. Absolute quantitation of a given peptide or the protein it is derived from may be achieved by comparing the SRM/MRM signature peak area for a given fragment peptide from the KRT5, KRT7, NapsinA, TTF1, TP63, and/or MUC1 proteins in an individual biological sample to the SRM/MRM signature peak area of an internal fragment peptide standard spiked into the protein lysate from the biological sample.

The internal standard can be a labeled synthetic version of the fragment peptide from the KRT5, KRT7, NapsinA, TTF1, TP63, and/or MUC1 proteins that is being interrogated (or a protein or polypeptide comprising the labeled synthetic version of the fragment peptide that is released upon proteolysis). The standard is spiked into a sample in known amounts, and the SRM/MRM signature peak area can be determined for both the internal fragment peptide standard and the native fragment peptide in the biological sample separately, followed by comparison of both peak areas.

This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.

Assessment of KRT5, KRT7, NapsinA, TTF1, TP63, and MUC1 protein levels in tissues based on analysis of formalin fixed patient-derived or subject-derived tissue can provide diagnostic, prognostic, and therapeutically-relevant information about each particular patient or subject. Described herein is a method for measuring the levels of the KRT5, KRT7, NapsinA, TTF1, TP63, and/or MUC1 proteins in a biological sample, comprising detecting and/or quantifying the amount of one or more modified or unmodified KRT5, KRT7, NapsinA, TTF1, TP63, and MUC1 protein fragment peptides in a protein digest prepared from said biological sample using mass spectrometry; and calculating the level of modified or unmodified KRT5, KRT7, NapsinA, TTF1, TP63, and/or MUC1 proteins in said sample; and wherein said level is a relative level or an absolute level. In a related embodiment, quantifying one or more KRT5, KRT7, NapsinA, TTF1, TP63, and MUC1 protein fragment peptides comprises determining the amount of the each of the KRT5, KRT7, NapsinA, TTF1, TP63, and MUC1 protein fragment peptides in a biological sample by comparison to an added internal standard peptide of known amount, wherein each of the KRT5, KRT7, NapsinA, TTF1, TP63, and MUC1 protein fragment peptides in the biological sample is compared to an internal standard peptide having the same amino acid sequence. In some embodiments the internal standard is an isotopically labeled internal standard peptide comprises one or more heavy stable isotopes selected from $^{18}O$, $^{17}O$, $^{34}S$, $^{15}N$, $^{13}C$, $^{2}H$ or combinations thereof.

The method for measuring levels of the KRT5, KRT7, NapsinA, TTF1, TP63, and/or MUC1 proteins in a biological sample described herein (or fragment peptides as surrogates thereof) may be used as a diagnostic indicator of cancer in a patient or subject. In one embodiment, the results from measurements of levels of the KRT5, KRT7, NapsinA, TTF1, TP63, and/or MUC1 proteins may be employed to determine the diagnostic stage/grade/status of a cancer by correlating (e.g., comparing) the levels of KRT5, KRT7, NapsinA, TTF1, TP63, and/or MUC1 proteins found in a tissue with the levels of KRT5, KRT7, NapsinA, TTF1, TP63, and/or MUC1 proteins found in normal and/or cancerous or precancerous tissues.

The only current method in use for detecting levels of specific proteins in formalin fixed patient tissue is immunohistochemistry (IHC). This method analyzes only one protein at a time on a single tissue section from a patient tumor tissue sample. So in order to analyze multiple proteins, multiple tissue sections must be interrogated which costs much time and labor. IHC uses an antibody to detect the presence of the target protein and because of the potential for non-specific binding of the antibody to proteins there is great inherent potential for signal background in any IHC experiment. In addition, IHC is only semi-quantitative at best. Due to these problems IHC fails to provide for objective quantitative analysis of multiple proteins simultaneously. The current embodiment is able to provide for objective quantitation of the KRT5, KRT7, NapsinA, TTF1, TP63, and/or MUC1 proteins simultaneously with 100% assay specificity utilizing a single section of a patient tissue sample saving significant time and money while providing for much more valuable data about expression of the KRT5, KRT7, NapsinA, TTF1, TP63, and/or MUC1 proteins.

This multiplex SRM/MRM assay can also include simultaneous analysis of other additional proteins beyond the KRT5, KRT7, NapsinA, TTF1, TP63, and/or MUC1 proteins, including drug target proteins such as EGFR, IGF-1R, and cMet. This is a valuable because analysis of additional proteins permits not only a determination of NSCLC type (ADC or SCC) and thus provides an indication whether a subject should receive either pemetrexed or bevacizumab, but it also indicates which additional drugs utilized in combination with pemetrexed and bevacizumab could be a useful to treating NSCLC. Examples additional drugs based on analysis of these additional drug target proteins include Erbitux, which targets the EGFR receptor, Figitumumab, which targets IGF-1R, and Foretinib, which targets c-Met and vascular endothelial growth factor receptor 2 (VEGFR-2).

Because both nucleic acids and protein can be analyzed from the same Liquid Tissue™ biomolecular preparation it is possible to generate additional information about disease diagnosis and drug treatment decisions from the nucleic acids in same sample upon which proteins were analyzed. For example, if the KRT5, KRT7, NapsinA, TTF1, TP63, and/or MUC1 proteins are expressed by certain cells at increased levels, when assayed by SRM the data can provide information about the state of the cells and their potential for uncontrolled growth, potential drug resistance and the development of cancers can be obtained. At the same time, information about the status of the KRT5, KRT7, NapsinA, TTF1, TP63, and MUC1 genes and/or the nucleic acids and proteins they encode (e.g., mRNA molecules and their expression levels or splice variations) can be obtained from nucleic acids present in the same biomolecular preparation. In one embodiment, information about the KRT5, KRT7, NapsinA, TTF1, TP63, and/or MUC1 proteins and/or one, two, three, four or more additional proteins may be assessed by examining the nucleic acids encoding those proteins. Those nucleic acids can be examined, for example, by one or more, two or more, or three or more of: sequencing methods, polymerase chain reaction methods, restriction fragment polymorphism analysis, identification of deletions, insertions, and/or determinations of the presence of mutations, including but not limited to, single base pair polymorphisms, transitions, transversions, or combinations thereof.

EXAMPLES

Example 1

Levels of KRT7, NapsinA, TTF1, MUC1, KRT5, and TP63 Observed in Adenocarcinoma and Squamous Cell Carcinoma Formalin fixed lung tissue specimens from four patients diagnosed with adenocarcinoma and four patients diagnosed with squamous cell carcinoma were obtained. Each sample was proteolytically digested with trypsin using the Liquid Tissue protocol provided in U.S. Pat. No. 7,473,532. The resulting lysate was subject to mass spectrometry analysis using internal standards that were isotope labeled, but otherwise chemically identically to the peptides whose intensity was determined in the mass spectrometer. The data resulting from the analysis of the lysates for KRT7, NapsinA, TTF1, MUC1, KRT5, and TP63 is shown in the histograms in FIG. 1. Histograms one through four (1-4) show data obtained from tissue samples of patients with adenocarcinoma, and histograms five through eight (5-8) show data obtained from patients with squamous cell carcinoma. Each set of histograms shows, from left to right, the amount of KRT7, NapsinA, TTF1, MUC1, KRT5, and TP63 given in attomoles/microgram of protein (amol/µg). The data is also presented numerically in Table 4

TABLE 4

| Diagnosis | KRT7 (amoles/µg) | NapsinA (amoles/µg) | TTF1 (amoles/µg) | MUC1 (amoles/µg) | KRT5 (amoles/µg) | TP63 (amoles/µg) |
|---|---|---|---|---|---|---|
| Adenocarcinoma | 51000.00 | 122680.00 | 974.33 | 2447.17 | 570.00 | 0 |
| Adenocarcinoma | 79000.00 | 103450.00 | 948.50 | 1471.33 | 720.00 | 0 |
| Adenocarcinoma | 82000.00 | 69150.00 | 738.17 | 4008.33 | 420.00 | 0 |
| Adenocarcinoma | 46000.00 | 132600.00 | 932.50 | 5330.00 | 1420.00 | 0 |
| Squamous Cell Carcinoma | 740.00 | 1030.00 | 0.00 | 0.00 | 221000.00 | 377.40 |
| Squamous Cell Carcinoma | 0.00 | 0.00 | 0.00 | 0.00 | 8868.00 | 201.10 |
| Squamous Cell Carcinoma | 0.00 | 0.00 | 0.00 | 0.00 | 176120.00 | 955.67 |
| Squamous Cell Carcinoma | 1340.00 | 1040.00 | 0.00 | 0.00 | 70070.00 | 512.70 |
| Squamous Cell Carcinoma | 740.00 | 1030.00 | 0.00 | 0.00 | 221000.00 | 377.40 |

The above description and exemplary embodiments of methods and compositions are illustrative of the scope of the present disclosure. Because of variations which will be apparent to those skilled in the art, however, the present disclosure is not intended to be limited to the particular embodiments described above.

The invention claimed is:

1. A method for measuring the level of the MUC1 protein in a human biological sample of formalin-fixed tissue, comprising detecting and quantifying the amount of a MUC1 protein fragment peptide in a protein digest prepared from said biological sample, using mass spectrometry; and calculating the level of MUC1 protein in said sample; wherein the MUC1 peptide is the peptide of SEQ ID NO:6, and
wherein said amount is a relative amount or an absolute amount.

2. The method of claim 1, further comprising the step of fractionating said protein digest prior to detecting and quantifying the amount of said MUC1 protein fragment peptide.

3. The method of claim 1, wherein said protein digest comprises a protease digest.

4. The method of claim 1, wherein said mass spectrometry comprises triple quadrupole mass spectrometry.

5. The method of claim 1, wherein quantifying the MUC1 protein fragment peptide comprises comparing the amount of said MUC1 protein fragment peptide in one biological sample to the amount of the same MUC1 protein fragment peptide in a different and separate biological sample.

6. The method of claim 1, wherein quantifying said MUC1 protein fragment peptide comprises determining the amount of said MUC1 protein fragment peptide in a biological sample by comparison to an added internal standard peptide of known amount, wherein said MUC1 protein fragment peptide in the biological sample is compared to an internal standard peptide having the same amino acid sequence.

7. The method of claim 6, wherein the internal standard peptide is an isotopically labeled peptide.

8. The method of claim 1, wherein detecting and quantifying the amount of said MUC1 protein fragment peptide in the protein digest indicates the presence of modified or unmodified MUC1 protein and an association with cancer in a patient or subject.

9. The method of claim 8, further comprising correlating the results of said detecting and quantifying the amount of said MUC1 protein fragment peptide, or the amount of said MUC1 protein to the diagnostic stage/grade/status of the cancer.

10. The method of claim 9, wherein correlating the results of said detecting said quantifying the amount said MUC1 protein fragment peptide, or the amount of said MUC1 protein to the diagnostic stage/grade/status of the cancer is combined with detecting and/or quantifying the amount of other proteins or peptides from other proteins in a multiplex format to provide additional information about the diagnostic stage/grade/status of the cancer.

11. The method of claim 9, further comprising administering to a patient or subject from which said biological sample was obtained a therapeutically effective amount of a therapeutic agent, wherein the therapeutic agent and/or amount of the therapeutic agent administered is based upon the amount of said MUC1 protein fragment peptide or the amount of MUC1 protein.

12. The method of claim 11, wherein the treatment or the therapeutic agent is directed to cancer cells expressing MUC1 protein.

* * * * *